(12) United States Patent
Vishwakarma et al.

(10) Patent No.: US 10,202,374 B2
(45) Date of Patent: Feb. 12, 2019

(54) 6-ARYL-4-PHENYLAMINO-QUINAZOLINE ANALOGS AS PHOSPHOINOSITIDE-3-KINASE INHIBITORS

(71) Applicant: COUNCIL OF SCIENTIFIC & INDUSTRIAL RESEARCH, New Delhi (IN)

(72) Inventors: Ram Asrey Vishwakarma, Jammu (IN); Sandip Bibishan Bharate, Jammu (IN); Shashi Bhushan, Jammu (IN); Rammohan Rao Yadav, Jammu (IN); Santosh Kumar Guru, Jammu (IN); Prashant Joshi, Jammu (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/121,328

(22) PCT Filed: Feb. 16, 2015

(86) PCT No.: PCT/IN2015/000088
§ 371 (c)(1),
(2) Date: Aug. 24, 2016

(87) PCT Pub. No.: WO2015/128873
PCT Pub. Date: Sep. 3, 2015

(65) Prior Publication Data
US 2017/0015662 A1    Jan. 19, 2017

(30) Foreign Application Priority Data
Feb. 27, 2014  (IN) .............................. 554/DEL/2014

(51) Int. Cl.
| | | |
|---|---|---|
| *C07D 471/04* | (2006.01) | |
| *C07D 401/04* | (2006.01) | |
| *C07D 403/04* | (2006.01) | |
| *C07D 405/04* | (2006.01) | |
| *C07D 409/04* | (2006.01) | |
| *C07D 239/94* | (2006.01) | |

(52) U.S. Cl.
CPC ......... *C07D 471/04* (2013.01); *C07D 239/94* (2013.01); *C07D 401/04* (2013.01); *C07D 403/04* (2013.01); *C07D 405/04* (2013.01); *C07D 409/04* (2013.01)

(58) Field of Classification Search
CPC .................................................. C07D 401/01
See application file for complete search history.

(56) References Cited

U.S. PATENT DOCUMENTS 9,085,560 B2 *  7/2015  Ren ...................... C07D 401/14
2015/0030588 A1 *  1/2015  Jessen .................... C12Q 1/485
424/133.1

FOREIGN PATENT DOCUMENTS

| WO | WO96/16960     | *  | 6/1996  |
| WO | WO 96/16960    |    | 6/1996  |
| WO | WO 97/30034    | *  | 8/1997  |
| WO | WO 2008/009078 A2 | | 1/2008  |
| WO | WO 2008/157191 A2 | | 12/2008 |

OTHER PUBLICATIONS

Pinedo et al. (2000).*
McMahon et al. (2000).*
Neidle et al., "Cancer Drug Design and Discovery" (2008) pp. 427-431.*
International Search Report in connection with PCT International Application No. PCT/IN2015/000088.
Written Opinion of the International Searching Authority in connection with PCT International Application No. PCT/IN2015/000088.
Yadav et al. (2016), "6-Aryl substituted 4-(4-cyanomethyl) phenylamino quinazolines as a new class of isoform-selective PI3K-alpha inhibitors", European Journal of Medicinal Chemistry 122:731-743.

* cited by examiner

*Primary Examiner* — Paul V Ward
(74) *Attorney, Agent, or Firm* — John P. White; Cooper & Dunham LLP

(57) ABSTRACT

The present invention relates to 6-aryl-4-phenylamino quinazolines of formula I wherein, R and R' are as herein described. The present invention particularly relates to synthesis and anticancer and phoshpoinositide-3-kinase-α (PI3K-α) inhibitory activity. In addition, the invention relates to methods of using compounds for treating or preventing various cancers such as pancreatic, prostate, breast and melanoma.

16 Claims, 2 Drawing Sheets

6-ARYL-4-PHENYLAMINO-QUINAZOLINE ANALOGS AS PHOSPHOINOSITIDE-3-KINASE INHIBITORS

CROSS-REFERENCE TO RELATED APPLICATIONS

This application is a § 371 national stage of PCT International Application No. PCT/IN2015/000088, filed Feb. 16, 2015, claiming priority of Indian Patent Application No. 554/DEL/2014, filed Feb. 27, 2014, the content of each of which is hereby incorporated by reference into the application.

FIELD OF THE INVENTION

The present invention relates to 6-aryl-4-phenylamino quinazolines. The present invention particularly relates to synthesis, anticancer and phosphoinositide-3-kinase inhibitory activity of 6-aryl-4-phenylamino quinazoline compounds. More particularly the present invention relates to methods for the treatment of cancer diseases, including those caused by kinase-mediated proliferation of tumor cells. Compounds of the invention can be used for prevention or in the treatment of cancer diseases, such as pancreatic, breast, prostate and melanoma cancers.

BACKGROUND OF THE INVENTION

Cancer is an uncontrolled growth and spread of cells that may affect almost any tissue of the body. There are over 100 different types of cancer, and each is classified by the type of cell that is initially affected. The approach to the discovery of new anticancer drugs has recently evolved from a reliance on empiric cell-based screening for anti-proliferative effects to a more mechanistically based approach that targets the specific molecular lesions thought to be responsible for the development and maintenance of the malignant phenotype in various forms of cancer. Through this approach, the kinase inhibitors have emerged as a new class of anticancer drugs that are capable of directly interacting with the catalytic site of the target enzyme and thereby inhibiting kinase function or blocking kinase signaling. In 1994, Parke-Davis scientists reported the first generation of very potent kinase inhibitor with manifold selectivity against other kinases (Fry, D. V. et al., Science 1994, 265, 1093). This discovery spurred the development of projects throughout the pharmaceutical industry; and as of now 18 kinase inhibitors have been approved by FDA for various diseases, and more than 500 candidates are in active clinical development.

Phosphoinositide 3-kinases (PI3Ks) constitute a family of lipid kinases involved in the regulation of a network of signal transduction pathways that control a range of cellular processes (Ihle, N. T. and Powis, P. Mol. Cancer Ther. 2009, 8, 1; Vivanco, I. and Sawyers, C. L. Nature Rev. Cancer 2002, 2, 489). The PI3K signaling plays a central role in cellular processes critical for cancer progression, metabolism, growth, survival and motility. The PI3K family of enzymes is comprised of 15 lipid kinases with distinct substrate specificities, expression patterns, and modes of regulation. In particular, PI3K-α has emerged as an attractive target for cancer therapeutics. Significant efforts have been made to discover inhibitors of the PI3K pathway to treat cancers and several candidates have advanced to clinical studies such as XL-765 and XL-147 (Exelixis), which are class I PI3K inhibitors that have entered Phase I clinical studies for advanced solid tumors. Other PI3K inhibitors in clinical studies include BEZ-235 and BKM-120 (Phase II, Novartis) and GSK-1059615 (Phase I, GSK) for advanced solid tumors. AstraZeneca's AZD-6482, which is a PI3K-β inhibitor, has completed Phase I trials for the treatment of thrombosis. A quinazolinone-based isoform-specific PI3K-δ inhibitor CAL-101 (GS-1101, Gilead Sciences) is in Phase III and IC-87114 (Calistoga) has entered Phase I clinical trial. Other PI3K inhibitors in clinical trials include D106669 and D87503 (Phase I, Aeterna Zentaris), GDC-0941 (Phase I, Genentech) and PKI-587 (Phase I, Pfizer). In addition, several other PI3K inhibitors are in early stages of clinical trials.

Despite of the fact that large number of kinase inhibitors have received FDA-approval, the target selectivity remains a formidable challenge in drug development because almost all approved kinase inhibitor drugs works by competing with ATP for the ATP binding site of the enzyme. Hence, there is a great need for next-generation kinase inhibitors that work through alternative mechanisms such as allosteric inhibition. While recently approved kinase inhibitor drugs offer benefits for cancer treatment, further advances are required to effect tumor selective cell killing, avoid off-target related toxicities and improve survival rates (Bharate, S. B. et al., Chem. Rev. 2013, 113, 6761). Amongst the four isoforms of phosphoinositide 3-kinases, particularly the α-isoform has been found to be activated by mutation in several cancers; and therefore discovery of α-isoform selective inhibitor is highly important. BEZ-235 (Novartis molecule) is a pan-PI3K inhibitor inhibiting all four isoforms with $IC_{50}$ values of 4, 76, 7 and 5 nM respectively; thus showing very poor selectivity towards α-isoform compared with β, γ and δ isoforms (19, 17.5 and 1.25 fold selectivity).

OBJECTIVES OF THE INVENTION

The main object of the present invention is to provide 6-aryl-4-phenylamino quinazolines.

Another object of the present invention is to provide novel anticancer compounds for the treatment of various types of cancers, such as pancreatic, breast, prostate and melanoma cancer.

One more objective of the invention is to provide a process for preparation of 6-aryl-4-phenylamino quinazolines.

SUMMARY OF THE INVENTION

Accordingly, the present invention relates to a compound of formula I,

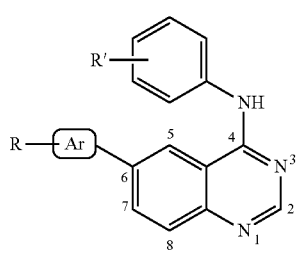

wherein, R is selected from the group comprising of hydrogen, alkyl, nitro, halogens (fluoro, chloro, bromo and iodo), formyl, allyl, vinyl, benzyl, acetyl, hydroxy, phenyl, substituted phenyl, fused aromatics;

R" is selected from the group consisting of hydrogen, cyanomethyl, or alkyls.

Ar is selected from the group comprising of aryl or heteroaryl, which is unsubstituted or substituted with an alkyl, nitro, halogens, formyl, allyl, vinyl, benzyl, acetyl, hydroxy, phenyl, substituted phenyl, fused aromatics.

In an embodiment of the invention wherein, aryl is selected from the group consisting of phenyl, biphenyl which is unsubstituted or substituted with different R groups, which is selected from the group comprising of alkyl, nitro, halogens (fluoro, chloro, bromo and iodo), formyl, allyl, vinyl, benzyl, acetyl, hydroxy, phenyl, substituted phenyl, fused aromatics. In another embodiment of the invention wherein Alkyl group is selected from the group consisting of (C1-C6)-alkyl, (C1-C4)-haloalkyl, (C1-C4)-alkoxy, (C1-C4)-haloalkoxy; or is (C5-C8)-cycloalkyl, (C5-C8)-cycloalkenyl, (C6-C10)-bicycloalkyl, (C6-C10)-bicycloalkenyl.

In yet another embodiment of the invention wherein, substituted phenyl is selected from the group consisting of alkylphenyls, alkoxyphenyls.

In one more embodiment of the invention wherein, fused aromatics is selected from the group consisting of naphthalene, 2,3-dihydrobenzo[b][1,4]dioxin, benzo[d][1,3]dioxol, benzofuran, benzo[b]thiophene, dibenzo(b,d)furan, dibenzo(b,d)thiophene, 1H-indole, quinoline, isoquinoline.

In still another embodiment of the invention wherein, heteroaryl is selected from the group consisting of pyridine, quinoline, isoquinoline, 2,3-dihydrobenzo[b][1,4]dioxin, benzo[d][1,3]dioxol, benzofuran, benzo[b]thiophene, dibenzo(b,d)furan, dibenzo(b,d)thiophene, 1H-indole.

In a further embodiment of the invention wherein, the structural formulae of the said compounds comprising:

6

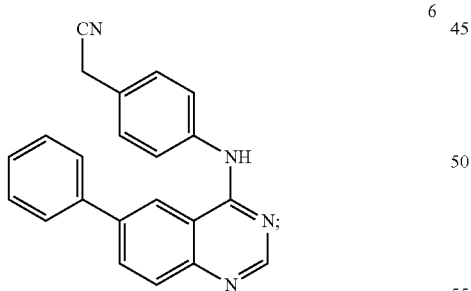

7

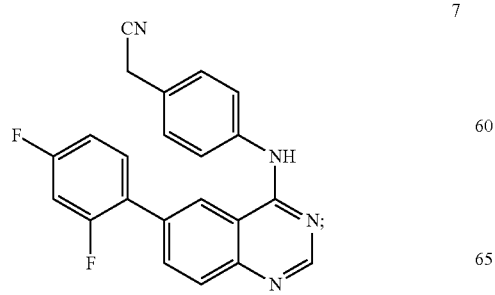

-continued

8

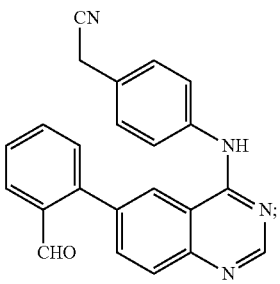

9

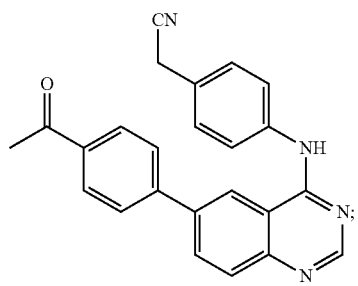

10

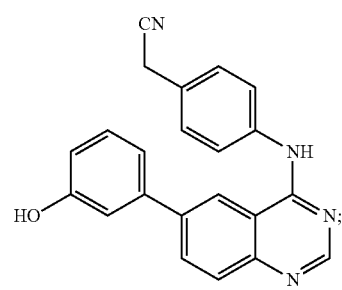

11

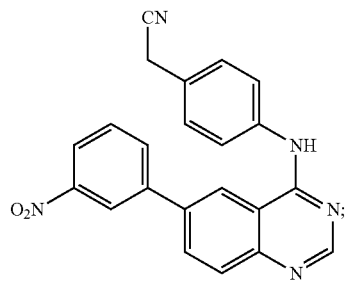

12

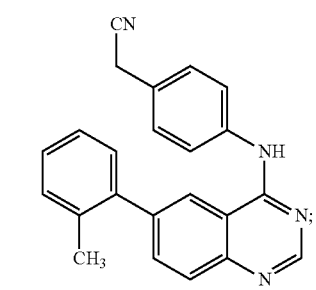

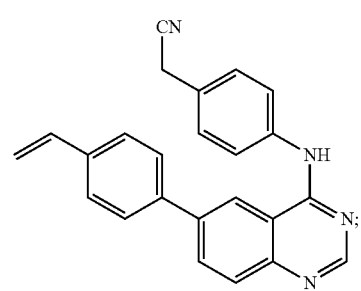
13
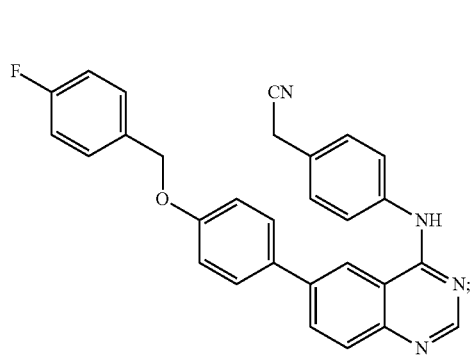
14
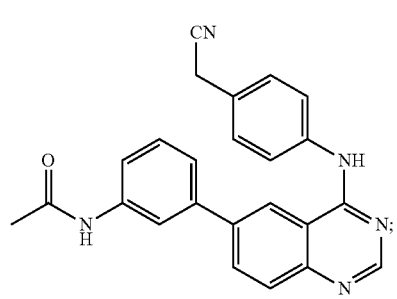
15
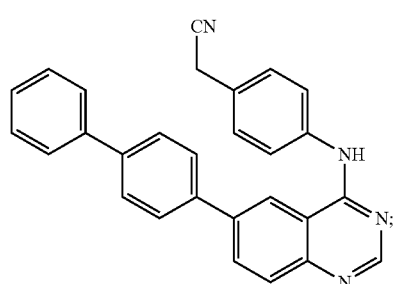
16
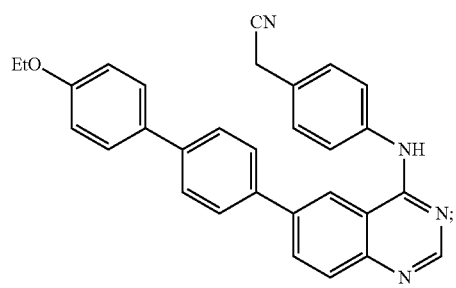
17
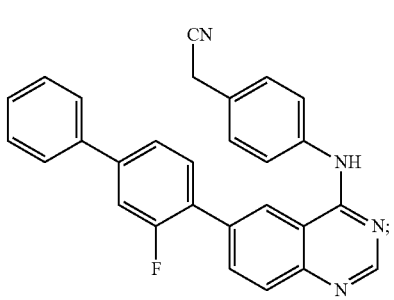
18
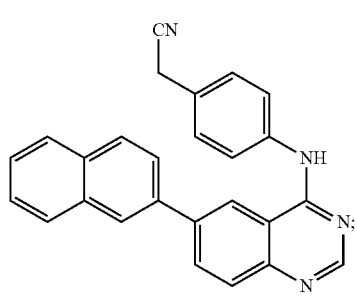
19
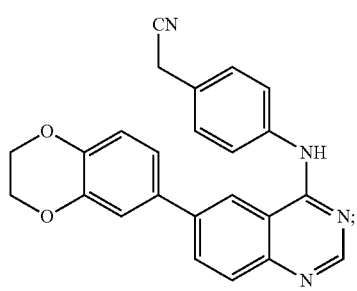
20
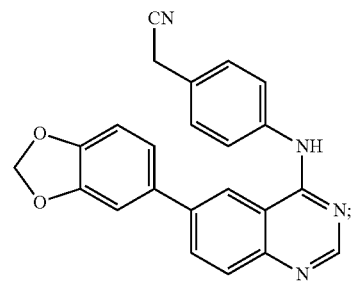
21
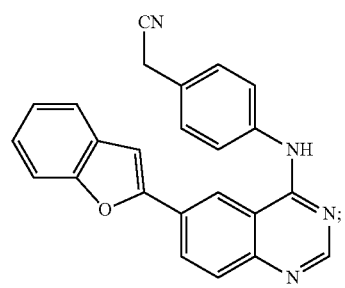
22

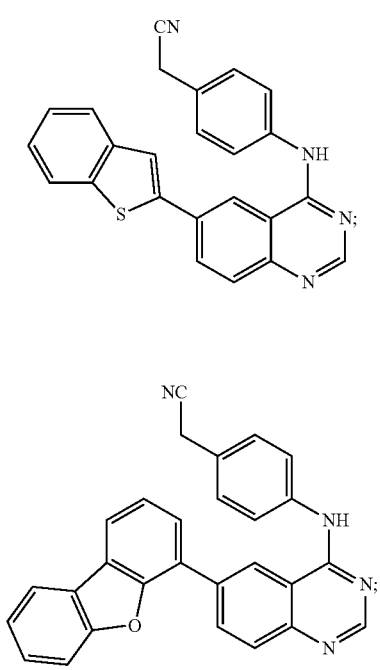

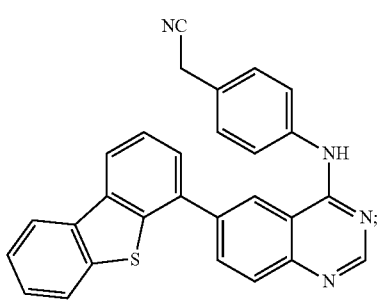

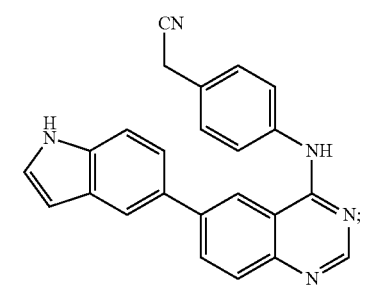

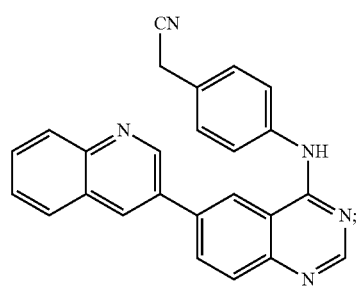

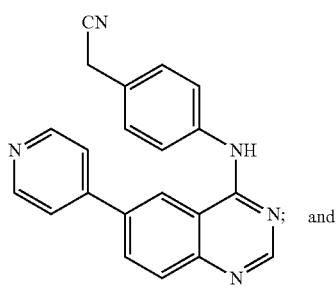

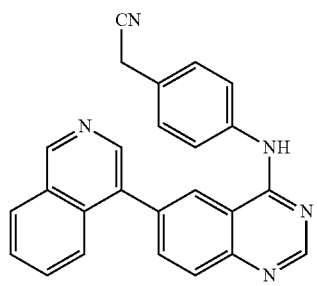

In still one more embodiment of the invention wherein, the compounds are useful for the treatment of cancer.

In an embodiment of the invention wherein, the compounds are phosphoinositide-3-kinase inhibitors.

In yet one more embodiment of the invention wherein the compounds are active against cancer cell lines selected from a group consisting of HL-60, A375, MCF-7, Panc-1, PC-3. In an embodiment of the invention wherein the compounds are phosphoinositide-3-α kinase inhibitors up to about 70% at 0.5 µM concentration.

Accordingly, the present invention provides a process for preparation of the compounds of general formula I, wherein the process steps comprising:

a) reacting anthralinic acid (1) with bromine in glacial acetic acid at a temperature in the range of 10-25° C. for the time period of ranging between 15-30 min, followed by diluting with dilute HCl to obtain monobromo anthranilic acid (2);

b) adding formamide to monobromo anthranilic acid obtained in step (a) followed by reflux at a temperature ranging between 100-150° C. for a time period ranging between 4-10 h to obtain compound 3;

c) adding $POCl_3$ to the solution of compound 3 as obtained in step (b) followed by reflux at a temperature ranging between 100-150° C. for a time period ranging between 4-10 h to obtain compound 4;

d) adding 4-amino benzylcyanide to the solution of compound 4 as obtained in step (c) forming a mixture which is dissolved in isopropanol followed by stirring for a time period of ranging between 2-6 h under reflux at a temperature ranging between 80-100° C. to obtain compound 5;

e) reacting aryl boronic acid in suitable solvent with compound 5 as obtained in step (d) followed by addition of $Pd(PPh_3)_4$ followed by stirring of the resultant mixture for the time period ranging between 12-24 h at a temperature ranging between 80-100° C. to yield compound of formula I.

In an embodiment of the invention wherein the aryl boronic acid used in step (e) is selected form the group consisting of substituted phenyls, substituted biphenyls, substituted naphthyls, substituted heteroaryls.

In a further embodiment of the invention wherein, the solvent used in step (e) is selected from toluene or dioxane.

In the present invention, we have identified 6-aryl-4-phenylamino quinazolines as PI3K-α isoform selective inhibitors showing selectivity fold up to >133, 56 and >49.7 versus β, γ and δ isoforms, respectively. Furthermore, the 6-aryl-4-phenylamino quinazoline scaffold has never been reported in literature as PI3K-alpha inhibitor

Synthetic scheme for preparation of 6-aryl-4-phenylamino-quinazoline analogs. Reagents and conditions: (a) $Br_2$ (1.2 equiv.), AcOH (10 mL), 10-25° C.; followed by dil.HCl (20 mL), reflux, 85%; (b) $NH_2CHO$ (4 equiv.), 150° C., 6 h, 70% (c) $POCl_3$ (5 mL), reflux at 100° C., 6 h, 92%; (d) 4-amino benzylcyanide (1.3 equiv), isopropanol (5 mL), reflux, 3 h, 82%; (e) $ArB(OH)_2$ (1.2 equiv.), $Pd(PPh_3)_4$ (0.05 equiv), 2 M $K_2CO_3$ solution (3 mL), dioxane (3 mL), reflux, 12 h, 43-92%.

Figure 1:
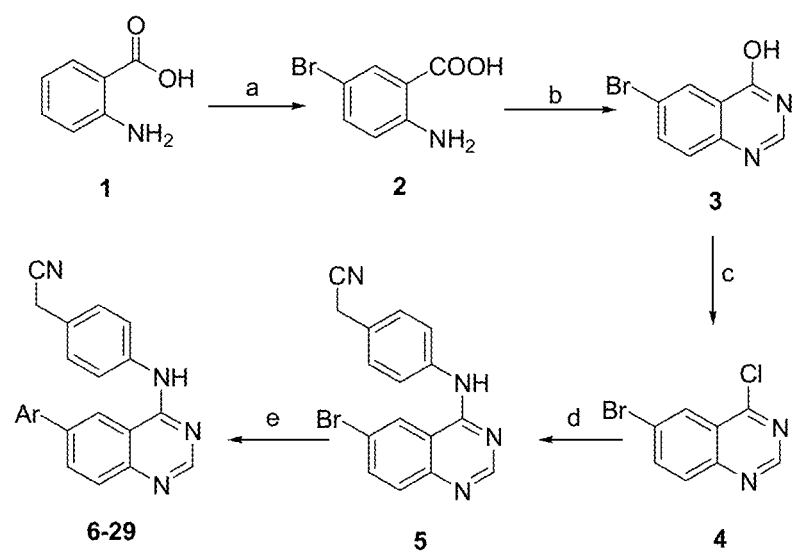
FIG. 1 is a diagram illustrating the chemical synthesis of the 6-aryl 4-phenylamino-quinazolines of the invention.
Figure 2:
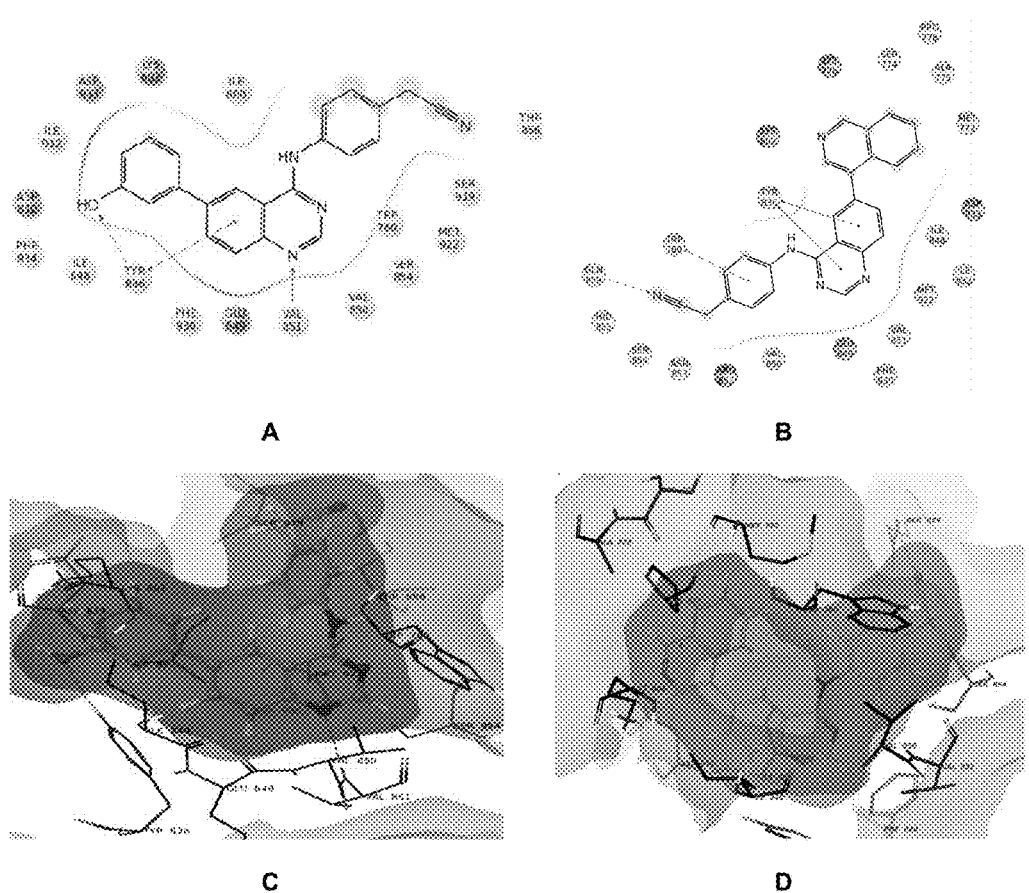

FIG. 2 is a diagram showing interactions of 6-aryl-4-phenylamino quinazoline 10 and 29 with the active site of phosphoinositide-3-kinase-α.

The 2D and 3D-representation of binding interactions of compounds 10 (A and C) and 29 (B and D) with PI3Kα. Red arrows and dotted line indicates sites of hydrogen bonding and solid green line indicates aromatic π-π interactions.

DETAILED DESCRIPTION OF THE INVENTION

The present invention relates to 6-aryl-4-phenylamino quinazoline compounds of general formula I as promising anticancer agents.

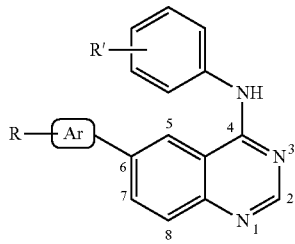

I

The present invention relates to novel compounds that shows promising anti-cancer activity against various cancer cell lines viz. Panc-1 (pancreatic cancer), MCF-7 (breast cancer), PC-3 (prostate cancer), HL-60 (leukemia) and A-375 (melanoma) and inhibition of phosphoinositide-3-kinase (PI3K-α) which is implicated in proliferation of tumor cells. The anticancer activity of 6-aryl-4-phenylamino quinazolines 10 ($IC_{50}$ values: 36 μM for panc-1, 15 μM for MCF-7, 37 μM for PC-3, 24 μM for HL-60 and 28 μM for A375) and 29 ($IC_{50}$ values: 9 μM for Panc-1, 12 μM for MCF-7, 9 μM for PC-3, 10 μM for HL-60 and 12 μM for A375) on various cancer cell lines is shown in Table 1 and 2. The compounds 10 and 29 showed promising inhibition of PI3K-α with $IC_{50}$ values of 0.115 and 0.150 μM, showing excellent selectivity towards α-isoform versus other isoforms of PI3K. Similarly, compound 26 displayed excellent selectivity towards α-isoform versus β- and δ-isoforms.

Unlike the known structurally similar PI3K-α inhibitor NVP-BEZ-235, which inhibits all isoforms of PI3K at low nanomolar concentrations, the compound 29 exhibited greater selectivity towards PI3K-α versus other isoforms. In particular, the compound 29 did not inhibit (0% inhibition) PI3K-β up to 20 μM. The isoform selectivity of compounds towards PI3K-α is provided in the Table 2. The promising activity of 6-aryl-4-phenylamino quinazolines 10, 26 and 29 against PI3K-α clearly indicates their potential to develop as anticancer agents. The complimentary fit of compounds 10 and 29 into the active site of PI3K-α is shown by the key H-bonding and π-π interactions of these compounds with active site residues of enzyme are shown in FIG. 2. The growth inhibitory properties of compounds of the invention against various cancer cell lines and their inhibitory activity against PI3K-α can therefore be used to treat or prevent diseases, disorders, conditions, or symptoms in a patient (e.g. human) that involve, directly, or indirectly, proliferation of cell growth or over-expression of PI3K-α kinase.

A class of 6-aryl-4-phenylamino quinazolines is presented and defined by structural formula I:

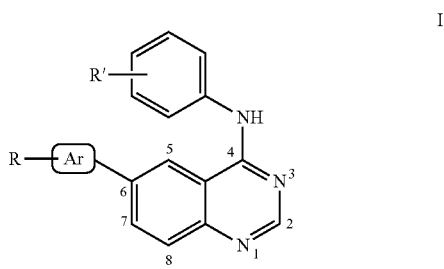

I wherein, the position 6 may contain various substituted aryl rings; and phenylamino moiety located at position 4 may be substituted; wherein Ar is aryl or heteroaryl, which is unsubstituted or substituted with an alkyl, nitro, halogens, formyl, allyl, vinyl, benzyl, acetyl, hydroxy, phenyl, substituted phenyl, fused aromatics.

wherein, aryl is selected from phenyl, biphenyl which is unsubstituted or substituted with different R groups.

Alkyl group is selected from (C1-C6)-alkyl, (C1-C4)-haloalkyl, (C1-C4)-alkoxy, (C1-C4)-haloalkoxy; or is (C5-C8)-cycloalkyl, (C5-C8)-cycloalkenyl, (C6-C10)-bicycloalkyl, (C6-C10)-bicycloalkenyl.

Substituted phenyl is selected from alkylphenyls, alkoxyphenyls.

Fused aromatics is selected from naphthalene, 2,3-dihydrobenzo[b][1,4]dioxin, benzo[d][1,3]dioxol, benzofuran, benzo[b]thiophene, dibenzo(b,d)furan, dibenzo(b,d)thiophene, 1H-indole, quinoline, isoquinoline.

Heteroaryl is selected from pyridine, quinoline, isoquinoline, 2,3-dihydrobenzo[b][1,4]dioxin, benzo[d][1,3]dioxol, benzofuran, benzo[b]thiophene, dibenzo(b,d)furan, dibenzo(b,d)thiophene, 1H-indole.

R is selected from hydrogen, alkyl, nitro, halogens, formyl, allyl, vinyl, benzyl, acetyl, hydroxy, phenyl, substituted phenyl, fused aromatics.

R' is selected from the group consisting of hydrogen, cyanomethyl, or any carbon atom which may be optionally substituted.

Compounds of the invention derived from Formula I include, but are not limited to, the following chemical structures:

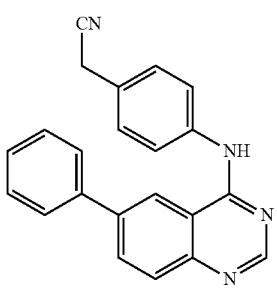 [SMILES: N#CCc1ccc(Nc2ncnc3ccc(-c4ccccc4)cc23)cc1]
6-phenyl-4-(4-cyanomethyl)phenylamino quinazoline (6)
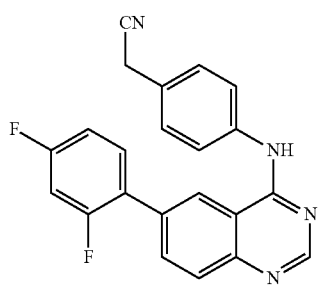 [SMILES: N#CCc1ccc(Nc2ncnc3ccc(-c4ccc(F)cc4F)cc23)cc1]
6-(2,4-difluorophenyl)-4-(4-cyanomethyl)phenylamino quinazoline (7)
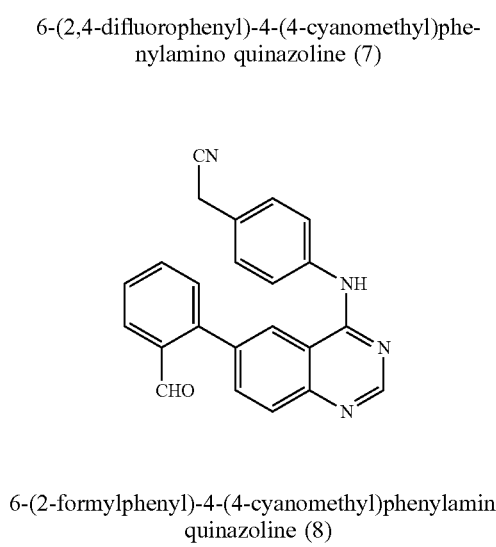
6-(2-formylphenyl)-4-(4-cyanomethyl)phenylamino quinazoline (8)
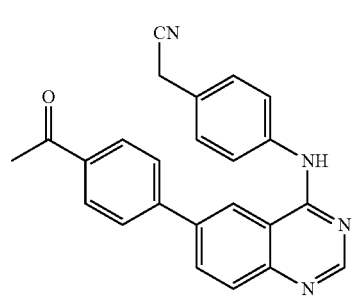 [SMILES: CC(=O)c1ccc(-c2ccc3ncnc(Nc4ccc(CC#N)cc4)c3c2)cc1]
6-(4-acetylphenyl)-4-(4-cyanomethyl)phenylamino quinazoline (9)
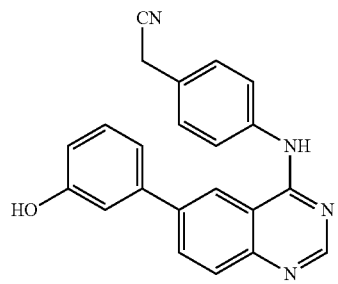 [SMILES: N#CCc1ccc(Nc2ncnc3ccc(-c4cccc(O)c4)cc23)cc1]
6-(3-hydroxyphenyl)-4-(4-cyanomethyl)phenylamino quinazoline (10)
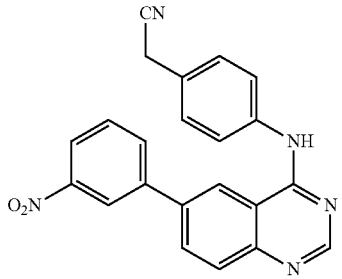 [SMILES: N#CCc1ccc(Nc2ncnc3ccc(-c4cccc([N+](=O)[O-])c4)cc23)cc1]
6-(3-nitrophenyl)-4-(4-cyanomethyl)phenylamino quinazoline (11)
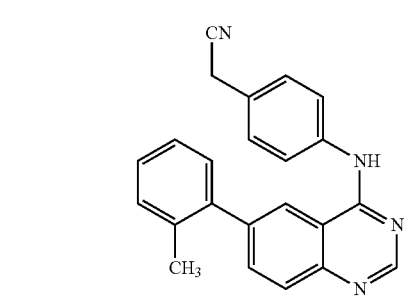 [SMILES: Cc1ccccc1-c1ccc2ncnc(Nc3ccc(CC#N)cc3)c2c1]

| 13 | 14 |
|---|---|
| 6-(2-methylphenyl)-4-(4-cyanomethyl)phenylamino quinazoline (12) | 6-(3-acetylaminophenyl)-4-(4-cyanomethyl)phenylamino quinazoline (15) |
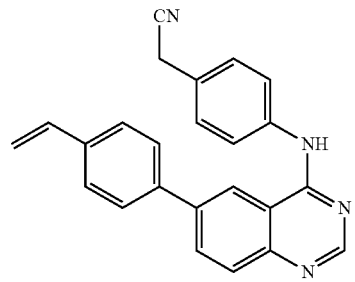 [SMILES: C=Cc1ccc(-c2ccc3ncnc(Nc4ccc(CC#N)cc4)c3c2)cc1]
6-(4-vinylphenyl)-4-(4-cyanomethyl)phenylamino quinazoline (13)
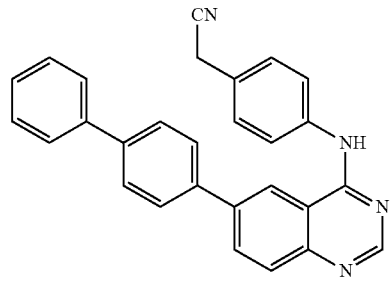
6-(4-phenylphenyl)-4-(4-cyanomethyl)phenylamino-quinazoline (16)
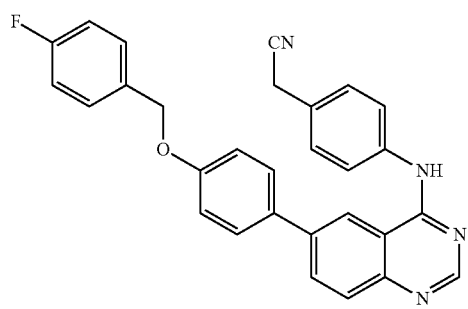 [SMILES: N#CCc1ccc(Nc2ncnc3ccc(-c4ccc(OCc5ccc(F)cc5)cc4)cc23)cc1]
6-(4-fluorobenzyloxyphen-4-yl)-4-(4-cyanomethyl) phenylamino quinazoline (14)
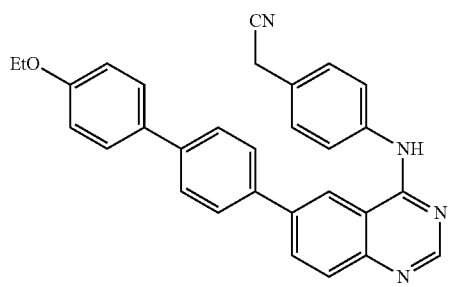
6-(4-(4-ethoxyphenyl)phenyl)-4-(4-cyanomethyl) phenylamino-quinazoline (17)
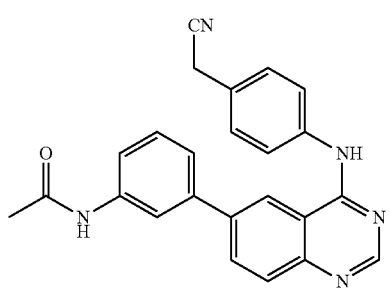 [SMILES: CC(=O)Nc1cccc(-c2ccc3ncnc(Nc4ccc(CC#N)cc4)c3c2)c1]
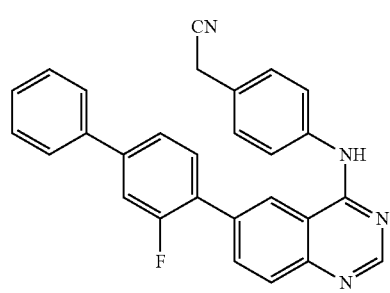 [SMILES: N#CCc1ccc(Nc2ncnc3ccc(-c4ccc(-c5ccccc5)cc4F)cc23)cc1]

6-(4-phenyl-2-fluorophenyl)-4-(4-cyanomethyl)phenylamino-quinazoline (18)
6-(benzo[d][1,3]dioxol-5-yl)-4-(4-cyanomethyl)phenylamino-quinazoline (21)
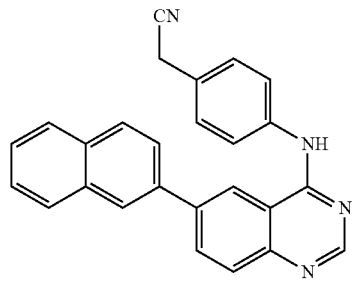 [SMILES: N#CCc1ccc(Nc2ncnc3ccc(-c4ccc5ccccc5c4)cc23)cc1]
6-(naphthalen-2-yl)-4-(4-cyanomethyl)phenylamino-quinazoline (19)
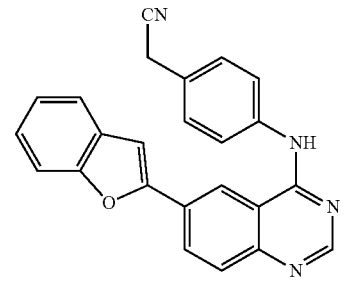
6-(benzofuran-2-yl)-4-(4-cyanomethyl)phenylamino-quinazoline (22)
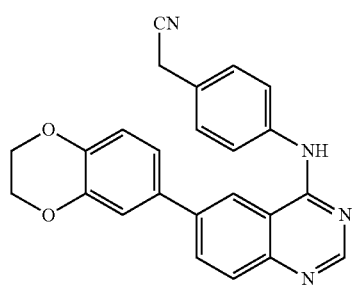 [SMILES: N#CCc1ccc(Nc2ncnc3ccc(-c4ccc5c(c4)OCCO5)cc23)cc1]
6-(2,3-dihydrobenzo[b][1,4]dioxin-6-yl)-4-(4-cyanomethyl)phenylamino-quinazoline (20)
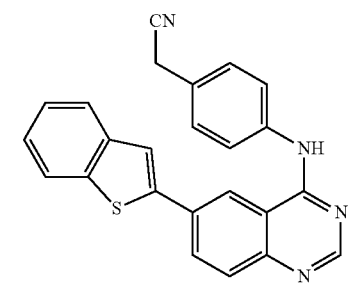
6-(benzo[b]thiophen-2-yl)-4-(4-cyanomethyl)phenylamino-quinazoline (23)
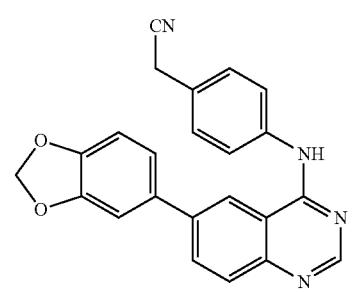 [SMILES: N#CCc1ccc(Nc2ncnc3ccc(-c4ccc5c(c4)OCO5)cc23)cc1]
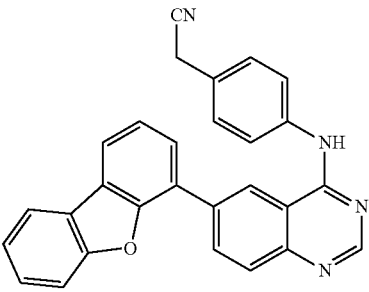 [SMILES: N#CCc1ccc(Nc2ncnc3ccc(-c4cccc5c4oc4ccccc45)cc23)cc1]

6-(dibenzo(b,d)furan-4-yl)-4-(4-cyanomethyl)phenylamino-quinazoline (24)

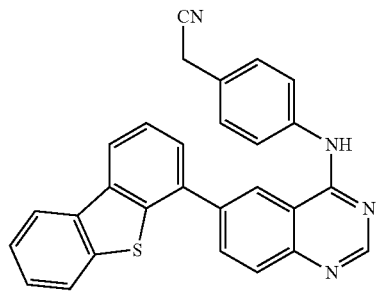 [SMILES: N#CCc1ccc(Nc2ncnc3ccc(-c4cccc5c4sc4ccccc45)cc23)cc1]

6-(dibenzo(b,d)thiophene-4-yl)-4-(4-cyanomethyl)phenylamino-quinazoline (25)

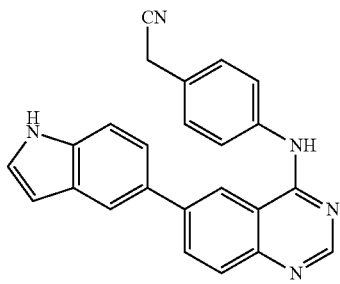 [SMILES: N#CCc1ccc(Nc2ncnc3ccc(-c4ccc5[nH]ccc5c4)cc23)cc1]

6-(1H-indol-5-yl)-4-(4-cyanomethyl)phenylamino-quinazoline (26)

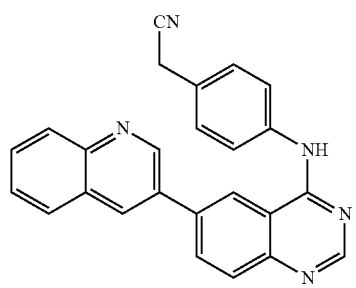 [SMILES: N#CCc1ccc(Nc2ncnc3ccc(-c4cnc5ccccc5c4)cc23)cc1]

6-(quinolin-3-yl)-4-(4-cyanomethyl)phenylamino-quinazoline (27)

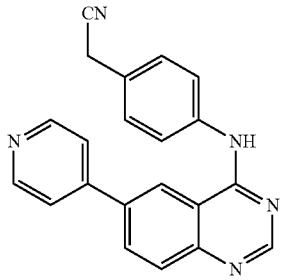 [SMILES: N#CCc1ccc(Nc2ncnc3ccc(-c4ccncc4)cc23)cc1]

6-(pyridin-4-yl)-4-(4-cyanomethyl)phenylamino-quinazoline (28); and

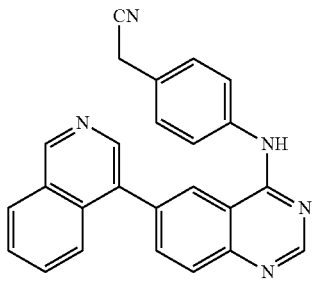 [SMILES: N#CCc1ccc(Nc2ncnc3ccc(-c4cncc5ccccc45)cc23)cc1]

6-(isoquinolin-4-yl)-4-(4-cyanomethyl)phenylamino-quinazoline (29)

As used herein, the terms below have the meanings indicated.

The term "alkoxy," as used herein, alone or in combination, refers to an alkyl ether radical, optionally substituted wherein the term alkyl is as defined below. Examples of alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical optionally substituted containing from 1 to 20 and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like.

The term "alkylamino" as used herein, alone or in combination, refers to an alkyl group optionally substituted attached to the parent molecular moiety through an amino group. Alkylamino groups may be mono- or dialkylated, forming groups such as, for example, N-methylamino, N-ethylamino, N,N-dimethylamino, N,N-ethylmethylamino and the like.

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl" as used herein, alone or in combination, means a carbocyclic aromatic system containing one, two or three rings wherein such rings may be attached together in a pendent manner or may be fused optionally substituted with at least one halogen, an alkyl containing from 1 to 3 carbon atoms, an alkoxyl, an aryl radical, a nitro function, a polyether radical, a heteroaryl radical, a benzoyl radical, an alkyl ester group, a carboxylic acid, a hydroxyl optionally protected with an acetyl or benzoyl group, or an amino function optionally protected with an acetyl or benzoyl group or optionally substituted with at least one alkyl containing from 1 to 12 carbon atoms.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstitutedsilyl, $N_3$, SH, $SCH_3$, $C(O)CH_3$, $CO2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term "cancer" as used herein refers to any disease, disorder, condition, or symptom characterized by overexpression of kinases. Cancer diseases include pancreatic, breast, prostate and melanoma cancer.

As used herein, reference to "treatment" of a patient is intended to include prophylaxis. The term "patient" means all mammals including humans. Examples of patients include humans, cows, dogs, cats, goats, sheep, pigs, rabbits, and rodents (e.g., rats, mice, and guinea pigs).

Cancer diseases. One or more compounds of the invention can be used to treat a patient (e.g. a human) at a risk of developing or already suffering from cancer disease, such as prostate, breast, pancreatic and melanoma cancer.

Methods of prevention and treatment. The compounds of the invention can be used to treat a patient (e.g. a human) that suffers from or is at a risk of suffering from a disease, disorder, condition, or symptom described herein. The compounds of the invention can be used alone or in combination with other agents and compounds in methods of treating or preventing e.g. a cancer disease (e.g. prostate cancer). Each such treatment described above includes the step of administering to a patient in need thereof a therapeutically effective amount of the compound of the invention described herein to delay, reduce or prevent such a disease, disorder, condition, or symptom. The compounds of the invention presented herein may be also useful in reducing growth inhibition of tumors.

It is understood that the foregoing examples are merely illustrative of the present invention. Certain modifications of the articles and/or methods employed may be, made and still achieve the objectives of the invention. Such modifications are contemplated as within the scope of the claimed invention.

EXAMPLES

Example 1

Synthesis of 2-amino-5-bromobenzoic acid (2)

Anthranilic acid (1, 1 g, 7.3 mmol) was dissolved in glacial acetic acid (10 mL) and cooled below 15° C. Then bromine (0.45 mL, 8.76 mmol) was added dropwise to the reaction mixture. The reaction mixture was converted to a thick mass of white glistening crystals consisting of the hydrobromides of the mono and dibromo anthranilic acids. The product was filtered off, washed with benzene and dried. It was then refluxed with dilute hydrochloric acid (20 mL) and filtered while hot under suction. The insoluble residue was extracted twice with boiling water (500 ml). The filtrate upon cooling yielded precipitate of the required monobromo anthranilic acid 2. Yield: 55%; light brown solid; m. p. 209-211° C.; $^1$H NMR ($CD_3OD$, 500 MHz): δ 7.87 (t, 1H, J=5.2 Hz), 7.31-7.28 (m, 1H), 6.67 (dd, 1H, J=5.0 Hz); ESI-MS: m/z 215 $[M+H]^+$.

Example 2

Synthesis of 6-bromoquinazolin-4-ol (3)

To the solution of 2-amino-5-bromobenzoic acid (2, 1 g, 4.63 mmol), formamide (0.74 mL, 18.52 mmol) was added and the resultant mixture was allowed to reflux at 150° C. for 6 h. After completion of reaction, the reaction mixture was filtered through Whatman filter paper and dried under vacuum to get the desired product 3 as a white solid. Yield: 70%, white solid, m. p. 209-211° C.; $^1$H NMR (DMSO-$d_6$, 500 MHz): δ 8.20 (d, 1H, J=2.3 Hz), 8.17 (d, 1H, J=6.1 Hz), 7.98-7.95 (m, 1H), 7.63 (d, 1H, J=8.7 Hz); HRMS: m/z 224.9633 calcd for $C_8H_6BrN_2O+H^+$ (224.9664).

Example 3

Synthesis of 6-bromo-4-chloroquinazoline (4)

To the solution of 6-bromoquinazolin-4-ol (3, 1 g, 4.44 mmol) in phosphoryl chloride (5 mL) was refluxed for 6 h at 120° C. The mixture was cooled to room temperature and poured into ice-water containing sodium bicarbonate to quench excess phosphoryl chloride. The mixture was extracted with dichloromethane (3×100 ml) and the solvent was evaporated to get the 6-bromo-4-chloroquinazoline 4 as a light yellow solid. Yield: 92%, light yellow solid, m. p. 273-275° C.; $^1$H NMR (CDCl$_3$, 500 MHz): δ 9.07 (s, 1H), 8.44 (d, 1H, J=2.0 Hz), 8.04 (d, 1H, J=2.0 Hz), 7.96 (d, 1H, J=8.9 Hz); HRMS: m/z 224.9633 calcd for C$_8$H$_6$BrN$_2$O+H$^+$ (224.9664).

Example 4

Synthesis of 6-bromo-4-(4-cyanomethyl)phenylamino quinazoline (5)

The mixture of 6-bromo-4-chloroquinazoline (4, 0.2 g, 0.83 mmol.) and 4-amino benzyl cyanide (0.142 g, 1.07 mmol) was dissolved in isopropanol (5 mL) and allowed to stir for 3 h under reflux at 80° C. After completion of reaction, the mixture was filtered through Whatman filter paper and dried under vacuum to get the desired product 5 as brown solid. Yield: 82%; brown solid; mp. 275-277° C., $^1$H NMR (DMSO-d$_6$, 400 MHz): δ 9.20 (s, 1H), 8.93 (s, 1H), 8.30-8.23 (m, 1H), 7.96-7.89 (m, 1H), 7.83-7.76 (m, 2H), 7.48 (d, 2H, J=7.2 Hz), 4.10 (s, 2H). $^{13}$C NMR (DMSO-d$_6$, 100 MHz): δ 158.71, 151.16, 138.71, 138.18, 135.91, 129.56, 128.43, 127.17, 124.96, 122.15, 120.86, 119.05, 115.01, 21.98. HRMS: m/z 339.0243 calcd for C$_{16}$H$_{12}$BrN$_4$+H$^+$ (339.0245).

Example 5

Synthesis of 6-phenyl-4-(4-cyanomethyl)phenylamino quinazoline (6) from 6-bromo-4-(4-cyanomethyl)phenylamino quinazoline and phenylboronic acid The solution of 2 M K$_2$CO$_3$(3 ml) in dioxane (3 ml) in round bottom flask was purged with nitrogen gas for 5 min at 25° C. To this solution, 6-bromo-4-(4-cyanomethyl)phenylamino quinazoline (5, 0.1 g, 1 mmol.) and phenylboronic acid (1.2 mmol) were added followed by addition of Pd(PPh$_3$)$_4$ (0.05 equiv.). The resulting reaction mixture was then stirred at 90° C. for 12 h. After completion of reaction, product was extracted with ethyl acetate (2×50 ml) and the combined organic layers were dried over anhydrous sodium sulphate to get crude product 6, which was purified by silica gel column chromatography. Yield: 81%, brick red solid, m.p. 253-255° C.; $^1$H NMR (DMSO-d$_6$, 400 MHz): δ 10.01 (s, 1H), 8.85 (s, 1H), 8.60 (s, 1H), 8.21 (d, 1H, J=8.5 Hz), 7.91-7.87 (m, 4H), 7.62-7.58 (m, 3H), 7.57-7.39 (m, 2H), 4.04 (s, 2H); IR (CHCl$_3$): vmax 3400, 2924, 2853, 1609, 1437, 1192, 1119 cm-1; HRMS: m/z 337.1452 calcd for C$_{22}$H$_{17}$N$_4$+H$^+$ (337.1453).

Example 6

Synthesis of 6-(2,4-difluorophenyl)-4-(4-cyanomethyl)phenylamino quinazoline (7) from 6-bromo-4-(4-cyanomethyl)phenylamino quinazoline and 2,4-difluorophenylboronic acid This compound was synthesized using the similar procedure as described in example 5. Yield: 45%; yellow solid; m. p. 186-188° C.; $^1$H NMR (CDCl$_3$, 400 MHz): δ 8.74 (s, 1H), 8.15 (s, 1H), 7.98-7.92 (m, 1H), 7.80 (d, 2H, J=8.8 Hz), 7.55-7.46 (m, 2H), 7.38 (d, 2H, J=8.4 Hz), 7.06-6.97 (m, 2H), 3.78 (s, 2H). $^{13}$C NMR (101 MHz, MeOD): δ 158.31, 154.55, 148.49, 138.13, 133.43, 132.12, 131.46, 128.40, 125.78, 123.13, 121.90, 117.86, 115.30, 111.76, 104.52, 104.26, 104.00, 22.72; IR (CHCl$_3$): v$_{max}$ 3391, 2955, 2923, 2854, 1606, 1574, 1532, 1515, 1495, 1424, 1401, 1269, 1142, 1101, 1020 cm$^{-1}$; HRMS: m/z 373.1258 calcd for C$_{22}$H$_{15}$F$_2$N$_4$+H$^+$ (373.1265).

Example 7

Synthesis of 6-(2-formylphenyl)-4-(4-cyanomethyl) phenylamino quinazoline (8) from 6-bromo-4-(4-cyanomethyl)phenylamino quinazoline and 2-formylphenylboronic acid This compound was synthesized using the similar procedure as described in example 5. Yield: 67%; brick red solid; m. p. 177-179° C.; $^1$H NMR (CDCl$_3$+1 drop of CD$_3$OD, 400 MHz): δ 9.99 (s, 1H), 8.80 (s, 1H), 8.32 (s, 1H), 8.12 (d, 1H, J=1.6 Hz), 8.01-8.97 (t, 2H, J=8.8 Hz), 7.84-7.76 (m, 3H), 7.71-7.62 (m, 1H), 7.56-7.46 (m, 2H), 7.43-7.39 (m, 1H), 7.36-7.30 (m, 1H), 3.74 (s, 2H); $^{13}$C NMR (101 MHz, CDCl$_3$+1 drop of CD$_3$OD): δ 192.32, 154.88, 148.58, 144.54, 136.48, 134.82, 134.00, 133.56, 131.95, 131.85, 131.14, 128.73, 128.60, 128.45, 128.42, 128.22, 127.45, 123.72, 123.41, 22.88; IR (CHCl$_3$): v$_{max}$ 3367, 2956, 2924, 2854, 2250, 1689, 1626, 1596, 1571, 1529, 1515, 1479, 1422, 1402, 1360, 1306, 1252, 1194, 1173, 1120, 1070, 1020 cm$^{-1}$; HRMS: m/z 365.1397 calcd for C$_{23}$H$_{17}$N$_4$O+H$^+$ (365.1402).

Example 8

Synthesis of 6-(4-acetylphenyl)-4-(4-cyanomethyl) phenylamino quinazoline (9) from 6-bromo-4-(4-cyanomethyl)phenylamino quinazoline and 4-acetylphenylboronic acid This compound was synthesized using the similar procedure as described in example 5. Yield: 45%; pale yellow solid; m. p. 157-159° C.; $^1$H NMR (CDCl$_3$+1 drop of CD$_3$OD, 400 MHz): δ 8.65 (d, 2H, J=9.0 Hz), 8.13-8.11 (t, 3H, J=1.6 Hz), 7.97-7.91 (m, 3H), 7.82 (d, 2H, J=8.0 Hz), 7.42 (s, 1H), 7.42 (m, 3H), 3.84 (s, 2H), (m, 2H), 2.70 (s, 3H); $^{13}$C NMR (126 MHz, DMSO): δ 197.59, 157.93, 154.87, 149.53, 143.38, 138.36, 136.63, 135.90, 132.05, 131.50, 131.42, 128.95, 128.80, 128.71, 128.26, 127.27, 126.57, 123.08, 121.20, 119.41, 115.33, 26.85, 21.90; IR (CHCl$_3$): v$_{max}$ 3369, 2953, 2924, 2855, 2250, 1738, 1678, 1603, 1572, 1532, 1515, 1423, 1362, 1265, 1020 cm$^{-1}$; HRMS: m/z 379.1555 calcd for C$_{24}$H$_{19}$N$_4$O+H$^+$ (379.1559).

Example 9

Synthesis of 6-(3-hydroxyphenyl)-4-(4-cyanomethyl)phenylamino quinazoline (10) from 6-bromo-4-(4-cyanomethyl)phenylamino quinazoline and 3-hydroxyphenylboronic acid This compound was synthesized using the similar procedure as described in example 5. Yield: 62%; pale yellow solid; m. p. 222-224° C.; $^1$H NMR (DMSO-d$_6$, 400 MHz): δ 10.01 (s, 1H), 9.65 (s, 1H), 8.81 (d, 1H, J=1.6 Hz), 8.59 (s, 1H), 8.14-8.11 (dd, 1H, J=2.0 & 1.6 Hz), 7.90-7.84 (m, 2H), 7.65-7.55 (m, 4H), 7.41-7.26 (m, 2H), 6.87-6.85 (m, 1H), 4.06 (s, 2H); $^{13}$C NMR (126 MHz, DMSO): δ 157.89, 154.35, 140.56, 138.49, 138.27, 132.04, 131.50, 131.42, 130.02, 128.79, 128.70, 128.21, 126.39, 122.97, 120.35, 119.41, 117.94, 115.28, 114.86, 114.02, 79.15, 21.89; IR (CHCl$_3$): v$_{max}$ 3400, 3055, 2955, 2924, 2854, 1731, 1591, 1484, 1437, 1400, 1275, 1219, 1189, 1119, 1072 cm$^{-1}$; HRMS: m/z 353.1402 calcd for C$_{22}$H$_{17}$N$_4$O+H$^+$ (353.1402).

Example 10

Synthesis of 6-(3-nitrophenyl)-4-(4-cyanomethyl) phenylamino quinazoline (11) from 6-bromo-4-(4-cyanomethyl)phenylamino quinazoline and 3-nitrophenylboronic acid This compound was synthesized using the similar procedure as described in example 5. Yield: 57%; pale yellow solid; m. p. 216-218° C.; $^1$H NMR (CDCl$_3$+1 drop of CD$_3$OD, 400 MHz): δ 8.69 (d, 1H, J=15.2 Hz), 8.28 (d, 1H, J=8.0 Hz), 8.14-8.27 (t, 1H, J=4.8 Hz), 7.97 (d, 1H, J=8.4 Hz), 7.83 (d, 1H, J=8.4 Hz), 7.75-7.71 (t, 1H, J=8.0 Hz), 7.65-7.58 (m, 2H), 7.53-7.49 (m, 2H), 7.42-7.36 (m, 3H), 3.83 (s, 2H); $^{13}$C NMR (101 MHz, DMSO-d$_6$) δ: 157.99, 154.97, 148.57, 140.80, 135.57, 133.66, 131.99, 131.79, 131.50, 131.40, 130.63, 128.78, 128.66, 128.26, 123.21, 122.59, 121.47, 121.36, 119.33, 21.92; IR (CHCl$_3$): v$_{max}$ 3400, 2955, 2923, 2853, 1733, 1606, 1536, 1423, 1384, 1157, 1021 cm$^{-1}$; HRMS: m/z 382.1302 calcd for C$_{22}$H$_{16}$N$_5$O$_2$+H$^+$ (382.1304).

Example 11

Synthesis of 6-(2-methylphenyl)-4-(4-cyanomethyl) phenylamino quinazoline (12) from 6-bromo-4-(4-cyanomethyl)phenylamino quinazoline and 2-methylphenylboronic acid This compound was synthesized using the similar procedure as described in example 5. Yield: 57%; orange solid; m. p. 173-175° C.; $^1$H NMR (CDCl$_3$, 400 MHz): δ 8.83-8.81 (t, 1H, J=2.4 Hz), 8.03-8.00 (t, 1H, J=9.6 Hz), 7.98-7.96 (t, 4H, J=6.0 Hz), 7.55 (s, 1H), 7.43-7.27 (m, 6H), 3.78 (d, 2H, J=6.0 Hz); $^{13}$C NMR (101 MHz, CDCl$_3$): δ 157.63, 154.73, 148.95, 140.83, 140.54, 138.33, 135.42, 134.63, 130.60, 129.79, 128.64, 128.37, 128.09, 126.06, 125.66, 122.52, 120.74, 117.97, 115.07, 23.14, 20.47; IR (CHCl$_3$): v$_{max}$ 3368, 2955, 2924, 2853, 2252, 1626, 1604, 1572, 1527, 1515, 1486, 1421, 1403, 1360, 1307, 1242, 1190, 1020 cm$^{-1}$; HRMS: m/z 351.1602 calcd for C$_{23}$H$_{19}$N$_4$+H$^+$ (351.1610).

Example 12

Synthesis of 6-(4-vinylphenyl)-4-(4-cyanomethyl) phenylamino quinazoline (13) from 6-bromo-4-(4-cyanomethyl)phenylamino quinazoline and 4-vinylphenylboronic acid This compound was synthesized using the similar procedure as described in example 5. Yield: 71%, pale yellow solid, m. p. 216-218° C.; $^1$H NMR (CDCl$_3$, 400 MHz): δ 8.66 (s, 1H), 8.42 (d, 1H, J=1.6 Hz), 8.07 (s, 1H), 7.92 (d, 1H, J=8.6 Hz), 7.82 (d, 2H, J=8.5 Hz), 7.73 (d, 2H, J=8.2 Hz), 7.56 (d, 3H, J=8.2 Hz), 7.40-7.34 (t, 1H, J=8.5 Hz), 6.80-6.77 (t, 1H, J=6.7 Hz), 5.85 (d, 1H, J=17.7 Hz), 5.33 (d, 1H, J=11.0 Hz), 3.81 (s, 2H); $^{13}$C NMR (126 MHz, DMSO-d$_6$): δ 158.30, 154.92, 149.57, 138.96, 138.87, 137.93, 137.19, 136.56, 132.05, 131.97, 128.89, 128.70, 127.72, 127.27, 126.90, 123.48, 120.64, 119.87, 115.83, 115.30, 22.39; IR (CHCl$_3$): v$_{max}$ 3368, 2951, 2923, 2857, 2248, 1741, 1623, 1603, 1571, 1514, 1497, 1423, 1360, 1020 cm$^{-1}$; HRMS: m/z 363.1605 calcd for C$_{24}$H$_{19}$N$_4$+H$^+$ (363.1610).

Example 13

Synthesis of 6-(4-fluorobenzyloxyphen-4-yl)-4-(4-cyanomethyl)phenylamino quinazoline (14) from 6-bromo-4-(4-cyanomethyl)phenylamino quinazoline and 4-((4-fluorobenzyl)oxy)phenylboronic acid This compound was synthesized using the similar procedure as described in example 5. Yield: 81%, pale yellow solid, m. p. 230-232° C.; $^1$H NMR (CDCl$_3$+1 drop of CD$_3$OD, 400 MHz): δ 8.65 (s, 1H), 8.45 (s, 1H), 8.04 (d, 1H, J=1.6 Hz), 7.88 (d, 1H, J=8.8 Hz), 7.81 (d, 2H, J=8.4 Hz), 7.73-7.70 (t, 2H, J=6.8 Hz), 7.48-7.38 (m, 5H), 7.13-7.08 (m, 4H), 5.12 (s, 2H), 3.82 (s, 2H); $^{13}$C NMR (126 MHz, DMSO-d$_6$): δ 158.70, 158.20, 154.60, 149.14, 139.03, 138.17, 132.18, 131.94, 130.45, 130.39, 128.77, 128.69, 126.82, 123.41, 119.93, 119.87, 115.84, 115.66, 69.04, 22.41; IR (CHCl$_3$): v$_{max}$ 3400, 2954, 2923, 2854, 1605, 1573, 1498, 1514, 1423, 1401, 1384, 1225, 1157, 1020 cm$^{-1}$; HRMS: m/z 461.1777 calcd for C$_{29}$H$_{22}$FN$_4$O+H$^+$ (461.1778).

Example 14

Synthesis of 6-(3-acetylaminophenyl)-4-(4-cyanomethyl)phenylamino quinazoline (15) from 6-bromo-4-(4-cyanomethyl)phenylamino quinazoline and 3-acetylaminophenylboronic acid This compound was synthesized using the similar procedure as described in example 5. Yield: 81%, pale yellow solid, m. p. 195-197° C.; $^1$H NMR (DMSO-d$_6$, 400 MHz): δ 10.01 (s, 2H), 8.80 (s, 1H), 8.60 (s, 1H), 8.10-8.07 (dd, 1H, J=1.6 & 0.8 Hz), 8.00 (s, 1H), 7.90-7.87 (dd, 3H, J=1.6 & 1.6 Hz), 7.66-7.46 (m, 4H), 7.39 (d, 2H, J=8.4 Hz), 4.04 (s, 2H), 2.07 (d, 3H, J=0.8 Hz); $^{13}$C NMR (126 MHz, DMSO-d$_6$): δ 168.40, 157.79, 154.38, 148.98, 139.85, 139.80, 138.43, 138.23, 131.42, 131.34, 129.30, 128.71, 128.61, 128.38, 128.14, 126.32, 122.87, 122.05, 120.57, 119.31, 118.50, 117.79, 115.26, 23.95, 21.83; IR (CHCl$_3$): v$_{max}$ 3368, 2921, 1676, 1608, 1534, 1515, 1480, 1426, 1119 cm$^{-1}$; HRMS: m/z 394.1668 calcd for C$_{24}$H$_{20}$N$_5$O+H$^+$ (394.1668).

Example 15

Synthesis of 6-(4-phenylphenyl)-4-(4-cyanomethyl) phenylamino-quinazoline (16) from 6-bromo-4-(4-cyanomethyl)phenylamino quinazoline and 4-phenylphenylboronic acid This compound was synthesized using the similar procedure as described in example 5. Yield: 57%, yellow solid, m. p. 214-216° C.; $^1$H NMR (DMSO-d$_6$, 400 MHz): δ 10.03 (s, 1H), 8.92 (d, 1H, J=1.6 Hz), 8.61 (s, 1H), 8.29-8.27 (m, 1H), 8.03 (d, 2H, J=8.4 Hz), 7.92-7.87 (m, 4H), 7.80-7.77 (t, 2H, J=1.2 Hz), 7.54-7.50 (t, 2H, J=7.6 Hz), 7.43-7.7.40 (m, 3H), 4.07-4.01 (m, 2H); $^{13}$C NMR (126 MHz, DMSO) δ 157.84, 154.47, 149.11, 139.59, 139.41, 138.46, 138.01, 137.98, 137.44, 131.64, 129.02, 128.47, 128.25, 127.69, 127.62, 127.25, 126.65, 123.03, 120.27, 119.42, 115.38, 21.90; IR (CHCl$_3$): v$_{max}$ 3401, 2953, 2927, 1604, 1567, 1515, 1486, 1423, 1358, 1021 cm$^{-1}$; HRMS: m/z 413.1769 calcd for C$_{28}$H$_{21}$N$_4$; found, 413.1766. HRMS: m/z 381.1357 calcd for C$_{23}$H$_{17}$N$_4$O$_2$+H$^+$ (381.1352).

Example 16

Synthesis of 6-(4-(4-ethoxyphenyl)phenyl)-4-(cyanomethyl)phenylamino-quinazoline (17) from 6-bromo-4-(cyanomethyl)phenylamino quinazoline and 4-(4-ethoxyphenyl)phenylboronic acid This compound was synthesized using the similar procedure as described in example 5. Yield: 47%, yellow solid, m. p. 195-197° C.; $^1$H NMR (CDCl$_3$, 400 MHz): δ 8.75 (s, 1H), 8.64 (s, 1H), 8.52 (s, 1H), 7.93 (d, 1H, J=8.8 Hz), 7.84-7.82 (m, 4H), 7.72 (d, 2H, J=8.4 Hz), 7.63-7.60 (t, 4H, J=4.4 Hz), 7.02 (d, 2H, J=8.4 Hz), 4.30 (d, 2H, J=6.8 Hz), 1.35-1.21 (m, 3H); IR (CHCl$_3$): v$_{max}$ 3306, 2956, 2925, 2855, 1729, 1604, 1568, 1515, 1494, 1424, 1401, 1360, 1252, 1190, 1082, 1019 cm$^{-1}$; HRMS: m/z 457.2012 calcd for C$_{30}$H$_{25}$N$_4$O+H$^+$ (457.2028).

Example 17

Synthesis of 6-(4-phenyl-2-fluorophenyl)-4-(4-cyanomethyl)phenylamino-quinazoline (18) from 6-bromo-4-(cyanomethyl)phenylamino quinazoline and 4-phenyl-2-fluorophenylboronic acid This compound was synthesized using the similar procedure as described in example 5. Yield: 57%, pale yellow solid, m. p. 229-231° C.; $^1$H NMR (CDCl$_3$+1 drop of CD$_3$OD, 400 MHz): δ 8.60 (d, 2H), 8.10 (d, 1H), 7.98-7.88 (m, 1H), 7.83 (d, 2H, J=8.4 Hz), 7.68-7.57 (m, 5H), 7.55-7.49 (m, 2H), 7.47-7.40 (m, 3H), 3.89 (s, 2H); $^{13}$C NMR (101 MHz, DMSO): δ 157.89, 154.72, 149.41, 140.38, 138.39, 136.01, 134.61, 131.46, 131.28, 128.76, 128.73, 128.68, 128.50, 128.24, 128.01, 126.55, 123.35, 123.08, 120.63, 119.33, 115.32, 21.93; IR (CHCl$_3$): vmax 3392, 2951, 2924, 2853, 2250, 1604, 1573, 1515, 1483, 1424, 1021 cm$^{-1}$; HRMS: m/z 431.1666 calcd for C$_{28}$H$_{20}$FN$_4$+H$^+$ (431.1672).

Example 18

Synthesis of 6-(naphthalen-2-yl)-4-(4-cyanomethyl)phenylamino-quinazoline (19) from 6-bromo-4-(4-cyanomethyl)phenylamino quinazoline and naphthalen-2-yl boronic acid This compound was synthesized using the similar procedure as described in example 5. Yield: 57%, pale yellow solid, m. p. 204-206° C.; $^1$H NMR (DMSO-d$_6$, 400 MHz): δ 10.04 (s, 1H), 8.97 (s, 1H), 8.64-8.59 (m, 1H), 8.47-8.33 (m, 1H), 8.14-7.87 (m, 6H), 7.60-7.53 (m, 3H), 7.45-7.37 (m, 2H), 4.08-4.03 (m, 2H); $^{13}$C NMR (126 MHz, DMSO-d$_6$) δ: 157.85, 154.48, 149.12, 136.42, 133.24, 132.34, 132.00, 131.46, 131.38, 128.75, 128.66, 128.56, 128.47, 128.20, 127.55, 126.59, 126.42, 126.39, 125.78, 125.28, 123.03, 120.69, 115.40, 21.89; IR (CHCl$_3$): v$_{max}$ 3369, 3053, 2955, 2924, 2854, 2250, 1733, 1603, 1572, 1529, 1515, 1468, 1422, 1404, 1385, 1360, 1245, 1175, 1119, 1070, 1020 cm$^{-1}$; HRMS: m/z 387.1611 calcd for C$_{26}$H$_{19}$N$_4$+H$^+$ (387.1610).

Example 19

Synthesis of 6-(2,3-dihydrobenzo[b][1,4]dioxin-6-yl)-4-(4-cyanomethyl)phenylamino-quinazoline (20) from 6-bromo-4-(4-cyanomethyl)phenylamino quinazoline and 2,3-dihydrobenzo[b][1,4]dioxin-6-yl boronic acid This compound was synthesized using the similar procedure as described in example 5. Yield: 81%, pale yellow solid, m. p. 207-209° C.; $^1$H NMR (DMSO-d$_6$, 400 MHz): δ 9.95 (s, 1H), 8.76 (d, 1H, J=1.6 Hz), 8.57 (s, 1H), 8.16-8.13 (dd, 1H, J=1.6 & 2.0 Hz), 7.89 (d, 2H, J=8.4 Hz), 7.82 (d, 1H, J=8.8 Hz), 7.65-7.53 (m, 1H), 7.46 (d, 1H, J=2.0 Hz), 7.41-7.37 (m, 3H), 7.03 (d, 1H, J=8.4 Hz), 4.32 (s, 4H), 4.05 (s, 2H); $^{13}$C NMR (126 MHz, DMSO-d$_6$): δ 157.72, 154.18, 148.75, 143.78, 143.55, 138.51, 137.46, 132.26, 131.49, 131.42, 128.78, 128.69, 128.20, 126.38, 123.00, 119.97, 119.50, 117.57, 115.60, 115.31, 64.23, 64.15, 21.90; IR (CHCl$_3$): v$_{max}$ 3854, 3745, 3400, 2922, 2853, 1602, 1514, 1495, 1422, 1307, 1249, 1068, 1021 cm$^{-1}$; HRMS: m/z 395.1508 calcd for C$_{24}$H$_{19}$N$_4$O$_2$+H$^+$ (395.1508).

Example 20

Synthesis of 6-(benzo[d][1,3]dioxol-5-yl)-4-(4-cyanomethyl)phenylamino-quinazoline (21) from 6-bromo-4-(4-cyanomethyl)phenylamino quinazoline and benzo[d][1,3]dioxol-5-yl boronic acid This compound was synthesized using the similar procedure as described in example 5. Yield: 57%, yellow solid, m. p. 241-243° C.; $^1$H NMR (DMSO-d$_6$, 400 MHz): δ 9.90 (s, 1H), 8.76 (d, 1H, J=1.6 Hz), 8.58 (s, 1H), 8.23-8.15 (m, 2H), 7.99-7.81 (m, 2H), 7.53 (d, 1H, J=1.6 Hz), 7.41-7.39 (t, 1H, J=6.4 Hz), 7.13-7.10 (t, 1H, J=6.4 Hz), 6.12 (s, 2H), 4.04 (s, 2H); $^{13}$C NMR (101 MHz, DMSO): δ 157.74, 154.21, 148.78, 148.13, 147.26, 138.52, 137.73, 133.28, 131.58, 131.50, 131.40, 128.78, 128.66, 128.25, 128.20, 126.38, 122.95, 120.85, 119.71, 119.33, 115.29, 108.74, 107.42, 101.32, 21.91; IR (CHCl$_3$): v$_{max}$ 3400, 2923, 1603, 1514, 1419, 1220, 1039 cm$^{-1}$; HRMS: m/z 381.1357 calcd for C$_{23}$H$_{17}$N$_4$O$_2$+H$^+$ (381.1352).

Example 21

Synthesis of 6-(benzofuran-2-yl)-4-(4-cyanomethyl)phenylamino-quinazoline (22) from 6-bromo-4-(4-cyanomethyl)phenylamino quinazoline and benzofuran-2-yl boronic acid This compound was synthesized using the similar procedure as described in example 5. Yield: 62%, pale yellow solid, m. p. 245-247° C.; $^1$H NMR (DMSO-d$_6$, 400 MHz): δ 10.14 (s, 1H), 9.09 (d, 1H, J=1.6 Hz), 8.61 (s, 1H), 8.41-8.38 (m, 1H), 7.93-7.88 (m, 2H), 7.75 (d, 1H, J=7.2 Hz), 7.71-7.69 (t, 1H, J=8.0 Hz), 7.65-7.7.60 (m, 1H), 7.58-7.53 (m, 1H), 7.42-7.39 (m, 2H), 7.32-7.30 (m, 1H), 4.06 (s, 2H); $^{13}$C NMR (126 MHz, DMSO): δ 157.84, 154.88, 154.57, 154.46, 149.84, 138.42, 132.77, 131.83, 131.46, 128.79, 128.70, 128.23, 125.09, 123.06, 119.29, 118.65, 114.73, 111.15, 103.34, 21.91; IR (CHCl$_3$): v$_{max}$ 3400, 2955, 2923, 2853, 1605, 1572, 1515, 1422, 1384, 1020 cm$^{-1}$; HRMS: m/z 377.1399 calcd for C$_{24}$H$_{17}$N$_4$O+H$^+$ (377.1402).

Example 22

Synthesis of 6-(benzo[b]thiophen-2-yl)-4-(4-cyanomethyl)phenylamino-quinazoline (23) from 6-bromo-4-(4-cyanomethyl)phenylamino quinazoline and benzo[b]thiophen-2-yl boronic acid This compound was synthesized using the similar procedure as described in example 5. Yield: 65%, yellow solid, m. p. 263° C., decomposed; $^1$H NMR (DMSO-d$_6$, 400 MHz): δ 10.04 (s, 1H), 8.91 (s, 1H), 8.58 (s, 1H), 8.26-8.23 (dd, 1H, J=2.0 & 2.0 Hz), 8.05-8.02 (t, 2H, J=6.8 Hz), 7.91-7.84 (m, 3H), 7.44-7.38 (m, 4H), 4.04-4.00 (t, 2H, J=8.0 Hz); $^{13}$C NMR (101 MHz, DMSO-d$_6$): δ 157.69, 154.65, 149.52, 142.35, 140.22, 138.89, 138.30, 131.42, 130.88, 128.63, 128.14, 126.51, 124.90, 124.86, 123.76, 123.09, 122.45, 121.09, 119.89, 119.25, 115.36, 21.85; IR (CHCl$_3$): ν$_{max}$ 3392, 2951, 2922, 2852, 1602, 1572, 1514, 1419, 1403, 1361, 1157, 1020, cm$^{-1}$; HRMS: m/z 393.1163 calcd for C$_{24}$H$_{17}$N$_4$S+H$^+$ (393.1174).

Example 23

Synthesis of 6-(dibenzo(b,d)furan-4-yl)-4-(4-cyanomethyl)phenylamino-quinazoline (24) from 6-bromo-4-(4-cyanomethyl)phenylamino quinazoline and dibenzo(b,d)furan-4-yl boronic acid This compound was synthesized using the similar procedure as described in example 5. Yield: 42%, pale yellow solid, m. p. 207-209° C.; $^1$H NMR (DMSO-d$_6$, 400 MHz): δ 10.03 (s, 1H), 9.02 (d, 1H, J=1.6 Hz), 8.66 (s, 1H), 8.47-8.45 (dd, 1H, J=1.6 & 2.0 Hz), 8.26-8.23 (m, 2H), 7.99 (d, 1H, J=8.8 Hz), 7.91 (d, 3H, J=8.0 Hz), 7.78 (d, 1H, J=8.0 Hz), 7.65-7.55 (m, 3H), 7.48-7.39 (m, 2H), 4.05 (s, 2H); $^{13}$C NMR (126 MHz, DMSO): δ 157.86, 155.49, 154.75, 152.58, 149.16, 138.47, 133.90, 133.61, 132.03, 131.49, 131.42, 128.78, 128.69, 128.23, 127.84, 127.58, 126.44, 124.47, 124.31, 123.72, 123.41, 123.32, 122.97, 122.62, 121.30, 120.92, 119.39, 115.36, 111.96, 21.91; IR (CHCl$_3$): ν$_{max}$ 3392, 2955, 2923, 2853, 1604, 1573, 1530, 1515, 1490, 1451, 1402, 1362, 1189, 1120, 1020 cm$^{-1}$; HRMS: m/z calcd for C$_{28}$H$_{19}$N$_4$O, 427.1553+H$^+$ (427.1559).

Example 24

Synthesis of 6-(dibenzo(b,d)thiophene-4-yl)-4-(4-cyanomethyl) phenylamino-quinazoline (25) from 6-bromo-4-(4-cyanomethyl) phenylamino quinazoline and dibenzo(b,d)thiophene-4-yl boronic acid This compound was synthesized using the similar procedure as described in example 5. Yield: 45%, pale yellow solid, m. p. 199-201° C.; $^1$H NMR (CDCl$_3$, 400 MHz): δ 8.80 (s, 1H), 8.36 (d, 1H, J=1.6 Hz), 8.19-8.11 (m, 3H), 8.03 (d, 1H, J=8.8 Hz), 7.80-7.77 (t, 1H, J=3.6 Hz), 7.57-7.46 (m, 4H), 7.36-7.30 (m, 2H), 3.72 (s, 2H). IR (CHCl$_3$): ν$_{max}$ 3392, 2922, 2853, 1605, 1571, 1537, 1514, 1421, 1026 cm$^{-1}$; HRMS: m/z 443.1320 calcd for C$_{28}$H$_{19}$N$_4$S+H$^+$ (443.1330).

Example 25

Synthesis of 6-(1H-indol-5-yl)-4-(4-cyanomethyl)phenylamino-quinazoline (26) from 6-bromo-4-(4-cyanomethyl)phenylamino quinazoline and 1H-indol-5-yl boronic acid This compound was synthesized using the similar procedure as described in example 5. Yield: 81%, dark yellow solid, m. p. 267-269° C.; $^1$H NMR (DMSO-d$_6$, 400 MHz): δ 11.23 (s, 1H), 9.99 (s, 1H), 8.83 (d, 1H, J=17.6 Hz), 8.57 (d, 1H, J=17.6 Hz), 8.24-8.22 (dd, 1H, J=2.0 & 1.6 Hz), 8.08 (s, 1H), 7.93-7.84 (dd, 3H, J=8.4 & 8.4 Hz), 7.66-7.53 (m, 3H), 7.44-7.39 (m, 2H), 6.54 (d, 1H, J=17.6 Hz), 4.05 (s, 2H); $^{13}$C NMR (126 MHz, DMSO-d$_6$): δ 157.70, 153.86, 148.37, 139.94, 138.63, 135.70, 131.50, 131.42, 130.21, 128.79, 128.70, 128.27, 128.19, 126.39, 126.25, 122.94, 120.72, 119.57, 119.43, 118.79, 111.91, 101.61, 21.90; IR (CHCl$_3$): ν$_{max}$ 3787, 3212, 2923, 2853, 1603, 1572, 1529, 1514, 1436, 1421, 1309, 1175, 1119, 1070 cm$^{-1}$; HRMS: m/z 376.1564 calcd for C$_{24}$H$_{18}$N$_5$+H$^+$ (376.1562).

Example 26

Synthesis of 6-(quinolin-3-yl)-4-(4-cyanomethyl)phenylamino-quinazoline (27) from 6-bromo-4-(4-cyanomethyl)phenylamino quinazoline and quinolin-3-yl boronic acid This compound was synthesized using the similar procedure as described in example 5. Yield: 62%, off-white solid, m. p. ° C.; $^1$H NMR (DMSO-d$_6$, 400 MHz): δ 10.06 (s, 1H), 9.52 (d, 1H, J=2.0 Hz), 9.10 (d, 1H, J=1.6 Hz), 8.86 (d, 1H, J=2.0 Hz), 8.64 (s, 1H), 8.45-8.42 (m, 1H), 8.12 (d, 2H, J=8.4 Hz), 7.97 (d, 3H, J=8.4 Hz), 7.91 (d, 1H, J=8.4 Hz), 7.83 (d, 1H, J=1.2 Hz), 7.42 (d, 2H, J=8.8 Hz), 4.05 (s, 2H); IR (CHCl$_3$): ν$_{max}$ 3400, 2922, 1617, 1423, 1130 cm$^{-1}$; HRMS: m/z 388.1559 calcd for C$_{25}$H$_{18}$N$_5$+H$^+$ (388.1562).

Example 27

Synthesis of 6-(pyridin-4-yl)-4-(4-cyanomethyl)phenylamino-quinazoline (28) from 6-bromo-4-(4-cyanomethyl)phenylamino quinazoline and pyridin-4-yl boronic acid This compound was synthesized using the similar procedure as described in example 5. Yield: 81%, pale yellow solid, m. p. 234-236° C.; $^1$H NMR (CDCl$_3$+1 drop of CD$_3$OD, 400 MHz): δ 8.62 (s, 3H), 8.11-8.09 (t, 1H, J=6.8 Hz), 7.97 (d, 1H, J=8.4 Hz), 7.83 (d, 4H, J=8.4 Hz), 7.41-7.32 (m, 3H), 3.81 (s, 2H). $^{13}$C NMR (CDCl$_3$+1 drop of CD$_3$OD, 126 MHz): δ 158.51, 154.91, 149.30, 147.56, 137.93, 135.52, 131.31, 128.13, 127.95, 125.94, 123.18, 121.70, 120.98, 117.80, 115.54, 22.50; IR (CHCl$_3$): ν$_{max}$ 3392, 2957, 2923, 2850, 1606, 1573, 1532, 1493, 1425, 1020 cm$^{-1}$; HRMS: m/z 338.1365 calcd for C$_{21}$H$_{16}$N$_5$+H$^+$ (338.1406).

Example 28

Synthesis of 6-(isoquinolin-4-yl)-4-(4-cyanomethyl)phenylamino-quinazoline (29) from 6-bromo-4-(4-cyanomethyl)phenylamino quinazoline and isoquinolin-4-yl boronic acid This compound was synthesized using the similar procedure as described in example 5. Yield: 57%, pale yellow solid, m. p. 237-239° C.; $^1$H NMR (DMSO-d$_6$, 400 MHz): δ 9.90 (s, 1H), 9.45 (s, 1H), 8.81 (s, 1H), 8.69 (s, 1H), 8.63 (s, 1H), 8.30 (d, 1H, J=8.0 Hz), 8.07-8.05 (dd, 1H, J=1.6 & 1.6 Hz), 7.97 (d, 1H, J=8.8 Hz), 7.92-7.77 (m, 4H), 7.38 (d, 2H, J=8.8 Hz), 3.36 (s, 2H); $^{13}$C NMR (126 MHz, DMSO): δ 157.76, 154.84, 152.44, 149.23, 142.99, 138.46, 134.75, 134.55, 133.22, 131.71, 131.45, 128.20, 128.20, 128.04, 127.97, 127.73, 126.36, 124.17, 124.10, 122.72, 119.35, 115.26, 21.89; IR (CHCl$_3$): v$_{max}$ 3400, 2923, 2853, 1624, 1423, 1042 cm$^{-1}$; HRMS: m/z 388.1564 calcd for C$_{25}$H$_{18}$N$_5$+H$^+$ (388.1562).

All examples disclosed in formula I, are prepared by employing the similar method containing different Ar, R, and R' groups, as described for preparation of compound 6 (example 5).

Example 29

Cytotoxicity of Compounds of the Invention

Compounds proposed in present invention were evaluated for their cytotoxic effect against panel of 5 cancer cell line viz. Panc-1 (pancreatic cancer), MCF-7 (breast cancer), PC-3 (prostate), HL-60 (leukemia) and A-375 (melanoma) using MTT assay. In each well of a 96-well plate, 3×10$^3$ cells were grown in 100 μL of medium. After 24 h, each test molecules were added to achieve a final concentration of 10 to 0.01 μmol/L, respectively. After 48 h of treatment, 20 μL of 2.5 mg/mL MTT (Organics Research, Inc.) solution in phosphate buffer saline was added to each well. After 48 h, supernatant was removed and formazan crystals were dissolved in 200 μL of DMSO. Absorbance was then measured at 570 nm using an absorbance plate reader (Bio-Rad Microplate Reader). Data are expressed as the percentage of viable cells in treated relative to non-treated conditions. Each experiment was repeated thrice and data was expressed as mean±SD of three independent experiments (Mordant, P. et al., *Mol. Cancer Ther.* 2010, 9, 358). Compounds showed promising cytotoxicity in panel of cell lines. Cytotoxicity results are shown in Table 1.

Example 30

Phosphoinositide-3-kinase Assay

Compounds proposed in present invention were evaluated for their inhibitory activity on phosphoinositide-3-kinase-alpha and other isoforms (beta, gamma and delta). The preliminary screening was performed at 0.5 μM concentration. The protocols used for these bioassays are as follows:

PI3K-α Assay: PI3K alpha (diluted in 12.5 mM Glycine-NaOH (pH 8.5), 50 mM KCl, 2.5 mM MgCl$_2$, 1 mM DTT, 0.05% CHAPS) is assayed in total volume of 20 ul containing 12.5 mM glycine-NaOH (pH 8.5), 50 mM KCl, 2.5 mM MgCl$_2$, 1 mM DTT, 0.05% CHAPS, 0.01 mM ATP and 0.05 mM diC8 PIP2. The enzyme is assayed for 80 min after which 20 ul of ADP-Glo reagent is added. After a further incubation of 40 min, 40 ul of Kinase Detection Buffer is added. The assays are incubated for 40 min and then read on PerkinElmer Envision for 1 sec/well.

PI3K-β Assay: PI3K beta (diluted in 12.5 mM glycine-NaOH (pH 8.5), 50 mM KCl, 2.5 mM MgCl$_2$, 1 mM DTT, 0.05% CHAPS) is assayed in total volume of 20 ul containing 12.5 mM Glycine-NaOH (pH 8.5), 50 mM KCl, 2.5 mM MgCl$_2$, 1 mM DTT, 0.05% CHAPS, 0.01 mM ATP and 0.05 mM diC8 PIP2. The enzyme is assayed for 60 min after which 20 ul of ADP-Glo reagent is added. After a further incubation of 40 min, 40 ul of kinase detection Buffer is added. The assays are incubated for 40 min and then read on PerkinElmer Envision for 1 sec/well.

PI3K-δ Assay: PI3K delta (diluted in 12.5 mM Glycine-NaOH (pH 8.5), 50 mM KCl, 2.5 mM MgCl$_2$, 1 mM DTT, 0.05% CHAPS) is assayed in total volume of 20 ul containing 12.5 mM Glycine-NaOH (pH 8.5), 50 mM KCl, 2.5 mM MgCl$_2$, 1 mM DTT, 0.05% CHAPS, 0.01 mM ATP and 0.05 mM diC8 PIP2. The enzyme is assayed for 120 min after which 20 ul of ADP-Glo reagent is added. After a further incubation of 40 min, 40 ul of Kinase Detection Buffer is added. The assays are incubated for 40 min and then read on PerkinElmer Envision for 1 sec/well.

PI3K-γ Assay: PI3K gamma (diluted in 12.5 mM Glycine-NaOH (pH 8.5), 50 mM KCl, 2.5 mM MgCl$_2$, 1 mM DTT, 0.05% CHAPS) is assayed in total volume of 20 ul containing 12.5 mM glycine-NaOH (pH 8.5), 50 mM KCl, 2.5 mM MgCl$_2$, 1 mM DTT, 0.05% CHAPS, 0.01 mM ATP and 0.05 mM diC8 PIP2. The enzyme is assayed for 75 min after which 20 ul of ADP-Glo reagent is added. After a further incubation of 40 min, 40 ul of Kinase Detection Buffer is added. The assays are incubated for 40 min and then read on PerkinElmer Envision for 1 sec/well.

The results of preliminary screening are shown in Table 1. The 6-aryl-4-phenylamino quinazolines 10, 21, 26, 28, and 29 showed >40% inhibition of PI3K-α at 0.5 μM. The IC$_{50}$ was determined for best compounds and results are shown in Table 2. The fold-selectivity of these compounds for PI3K-α isoform is also shown in Table 2.

Anticancer activity of 6-aryl-4-phenylamino quinazolines against pancreatic, breast, prostate, leukemia and melanoma cells; and inhibition of phosphoinositide-3-kinase-α (PI3K-α) by these compounds

TABLE 1

| Compound | Anticancer activity IC$_{50}$ (μM) | | | | | % Inhibition of PI3K-α at 0.5 μM |
|---|---|---|---|---|---|---|
| | HL-60 | A375 | MCF-7 | Panc-1 | PC-3 | |
| 6 | 32 | 24 | 23 | 40 | 27 | 16.4 |
| 7 | 7 | 9 | 10 | 21 | 28 | 17 |
| 8 | 42 | 39 | 91 | 90 | 21 | 1.3 |
| 9 | 28 | 32 | 45 | 13 | 24 | 44 |
| 10 | 24 | 28 | 15 | 36 | 37 | 69.9 |
| 11 | 15 | 23 | 12 | 7 | 29 | 38.1 |
| 12 | 36 | 32 | >100 | 68 | 38 | 4.1 |
| 13 | 16 | 27 | 11 | 32 | 34 | 36.4 |
| 14 | 14 | 16 | 12 | 13 | 13 | 11 |
| 15 | 23 | 38 | 14 | 38 | 26 | 36.8 |
| 16 | 16 | 13 | 29 | 30 | 10 | NI |
| 17 | 16 | 30 | 26 | 33 | 17 | NI |
| 18 | 16 | 32 | 13 | 33 | 14 | 20.3 |
| 19 | 25 | 31 | 16 | 48 | 22 | 8.2 |
| 20 | 21 | 27 | 34 | 32 | 34 | 33 |
| 21 | 27 | 24 | 34 | 33 | 7 | 48.6 |
| 22 | 17 | 10 | 9 | 28 | 8 | 29.8 |
| 23 | 14 | 14 | 8 | 24 | 13 | 2.7 |
| 24 | 12 | 36 | 27 | 31 | 16 | 1.5 |
| 25 | 31 | 34 | 34 | 33 | 18 | NI |
| 26 | 18 | 31 | 7 | 16 | 24 | 47.5 |
| 27 | 44 | 89 | 32 | 90 | 23 | NI |
| 28 | 32 | 35 | 32 | 39 | 76 | 45.6 |
| 29 | 10 | 12 | 12 | 9 | 9 | 48.8 |

NI, no inhibition at tested concentration; Panc-1: Human pancreatic carcinoma cell line; MCF-7: Human breast adenocarcinoma cell line; PC-3: human prostate cancer cell line; A-375: Human malignant melanoma cells; HL-60: Human leukemia cells; nd, not determined.

The IC$_{50}$ values for 6-aryl-4-phenylamino quinazolines against four isoforms of phosphoinositide-3-kinase and the fold-selectivity for PI3K-α isoform

TABLE 2

| Entry | Structure | PI3K inhibition (IC$_{50}$ values in μM) | | | | Fold-selectivity for PI3K-α with respect to other isoforms | | |
|---|---|---|---|---|---|---|---|---|
| | | -α | -β | -γ | -δ | -β | -γ | -δ |
| 9 | | 0.270 | >10 | 0.15 | >10 | >37 | 0.5 | >37 |
| 10 | | 0.115 | 0.67 | 1.84 | 0.27 | 5.8 | 16 | 2.3 |
| 11 | | 0.451 | >10 | 0.85 | >10 | >22.2 | 1.9 | >22.2 |
| 13 | | >10 | >10 | 0.52 | >10 | 1 | >0.05 | 1 |
| 15 | | 0.475 | >10 | 6.95 | >10 | >21 | 14.6 | >21 |

TABLE 2-continued

| Entry | Structure | PI3K inhibition (IC$_{50}$ values in μM) | | | | Fold-selectivity for PI3K-α with respect to other isoforms | | |
|---|---|---|---|---|---|---|---|---|
| | | -α | -β | -γ | -δ | -β | -γ | -δ |
| 20 | | 0.342 | >10 | 1.37 | >10 | >29.2 | 4 | >29.2 |
| 21 | | 0.321 | >10 | 0.19 | >10 | >31.1 | 0.6 | >31.1 |
| 26 | | 0.201 | >10 | 0.75 | >10 | >49.7 | 3.7 | >49.7 |
| 28 | | 0.704 | >10 | 0.36 | >10 | >14.2 | 0.5 | >14.2 |
| 29 | | 0.150 | >20 | 8.44 | 0.88 | >133 | 56 | 5.9 |

TABLE 2-continued

| | | PI3K inhibition (IC$_{50}$ values in μM) | | | | Fold-selectivity for PI3K-α with respect to other isoforms | | |
|---|---|---|---|---|---|---|---|---|
| Entry | Structure | -α | -β | -γ | -δ | -β | -γ | -δ |
| BEZ235 | 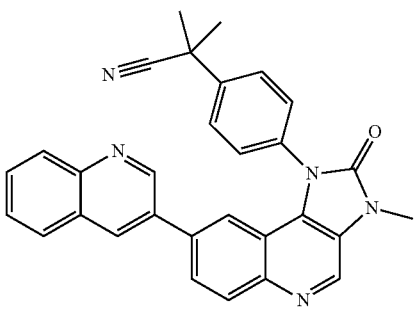 [SMILES: Cn1c(=O)n(-c2ccc(C(C)(C)C#N)cc2)c2c3cc(-c4cnc5ccccc5c4)ccc3ncc21] | 0.004 | 0.076 | 0.007 | 0.005 | 19 | 17.5 | 1.25 |

Among the examples depicted in Table 2, compound 29 displayed promising selectivity towards α-isoform versus β-isoform (>133 fold selectivity). Compound 29 also displayed 56-fold selectivity for α-isoform versus γ-isoform. Similarly, another compound 26 displayed >49.7 fold selectivity towards α-isoform versus β- and δ-isoforms. However, the Novartis molecule BEZ-235 has very weak selectivity towards α-isoform versus other three isoforms: β, γ and δ (19, 17.5 and 1.25 fold selectivity, respectively).

Example 31

Molecular Modeling Studies of 6-Aryl-4-phenylamino quinazolines 10 and 29 with phosphoinositide-3-kinase-α

The conformation, orientation and interactions of compounds 10 and 29 with phosphoinositide-3-kinase was determined by Glide module of Schrodinger molecular modeling package using PI3Kα (PDB: 2RD0) crystal structure (Huang, C.-H et al., Science 2007, 318, 1744). The interactions of inhibitors 10 and 29 with PI3Kα were studied by incorporating missing residues in the apo-form of PI3Kα (PDB: 2RD0). Protein was prepared by removing solvent, adding hydrogens and by minimizing energy using protein preparation wizard. Missing residues (Tyr307-Thr324, Ala415-Ala423, Phe506-Asp527 and Lys941-Glu950) were incorporated in the apo-form of PI3K-α (PDB: 2rD0) using Prime module (version 3.0) of Schrodinger Inc. LLC, NewYork, USA. Compounds were docked using Glide in extra-precision mode with up to three poses saved per molecule.

As depicted in FIG. 2, the compound 10 showed typical H-bonding interaction with the Val 851 residue of the hinge region and Tyr 836 residue of the ATP binding site. The phenolic ring of Tyr 836 residue stablizes the quinazoline ring via π-π interactions. Compound 29 showed H-bonding with the Gln859 residue of the PI3K-α catalytic domain instead of the Val851. Similar to compound 10, the phenolic Tyr-836 and indolyl Trp-780 stabilizes the quinazoline and phenolic ring of the compound 29 by aromatic π-π interactions. Both molecules fits into the hydrophobic cleft formed by Trp780, Tyr 836, Val 850, Val851, Ile 848, Phe 930, Ile932, Asp933 and Phe934 residues. The interaction map of compounds 10 and 29 in the active site of PI3K-α is shown in FIG. 2.

ADVANTAGES OF THE INVENTION

The main advantages of the present invention are:
Compounds of the invention show promising anticancer activity against various cancer cell lines and inhibit phosphoinositide-3-kinase-alpha, a key target in cancer at low micromolar to nanomolar concentrations.
Compounds of the invention are stable.

What is claimed is:
1. A compound of formula I,

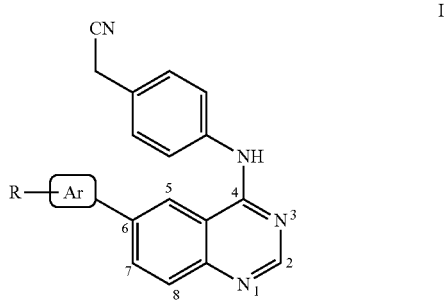

wherein Ar is phenyl, pyridine, quinoline, isoquinoline, naphthalene, 2,3-dihydrobenzo[b][1,4]dioxin, benzo[d][1,3]dioxol, benzofuran, benzo[b]thiophene, dibenzo(b,d)furan, dibenzo(b,d)thiophene or 1H-indole, each of which is unsubstituted or substituted with one or two R,
wherein R is alkyl, alkoxy, alkenyl, nitro, fluoro, chloro, bromo, iodo, formyl, allyl, vinyl, benzyl, acetyl, hydroxyl, phenyl, substituted phenyl, biphenyl, substituted biphenyl or a fused aromatic,
wherein the substituted phenyl is substituted with alkyl, alkoxy, alkenyl, nitro, fluoro, chloro, bromo, iodo, formyl, allyl, vinyl, benzyl, acetyl or hydroxy, and
the substituted biphenyl is substituted with alkyl, nitro, fluoro, chloro, bromo, iodo, formyl, allyl, vinyl, benzyl, acetyl or hydroxyl, and
the fused aromatic is naphthalene, 2,3-dihydrobenzo[b][1, 4]dioxin, benzo[d][1,3]dioxcl, benzofuran, benzo[b]thiophene, dibenzo(b,d)furan, dibenzo(b,d)thiophene, 1H-indole, quinoline or isoquinoline.
2. The compound of claim 1, wherein the Ar is selected from the group consisting of a phenyl which is unsubstituted or substituted with one or two R which are alkyl, alkoxy, alkenyl, nitro, fluoro, chloro, bromo, iodo, formyl, allyl, vinyl, benzyl, acetyl or hydroxy, and a biphenyl which is unsubstituted or substituted with one or two R which are alkyl, nitro, fluoro, chloro, bromo, iodo, formyl, allyl, vinyl, benzyl, acetyl, or hydroxyl.

3. The compound of claim 2, wherein the phenyl or the biphenyl are substituted with two R groups which are different from each other.

4. The compound of claim 1, wherein the alkyl is selected from the group consisting of (C1-C6)-alkyl, (C1-C4)-haloalkyl, (C1-(C5-C8)-cycloalkyl, and (C6-C10)-bicycloalkyl.

5. The compound of claim 1, wherein the alkoxy is (C1-C4)-alkoxy, or (C1-C4)-haloalkoxy.

6. The compound of claim 1, wherein the alkenyl is (C5-C8)-cycloalkenyl or (C6-C10)-bicycloalkenyl.

7. The compound of claim 1, wherein the substituted phenyl is an alkylphenyl or alkoxyphenyl.

8. The compound of claim 1, selected from one of the following:

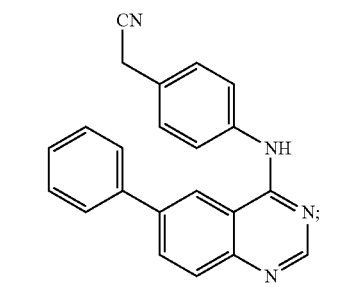
6

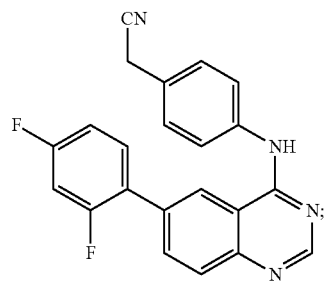
7

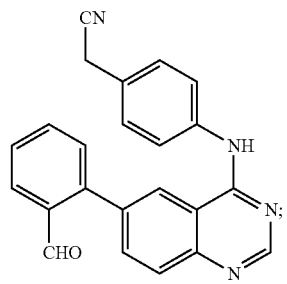
8

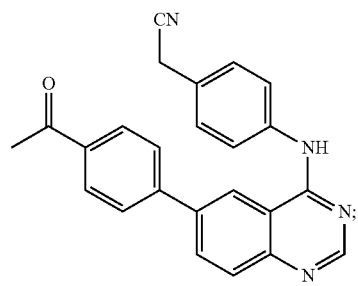
9

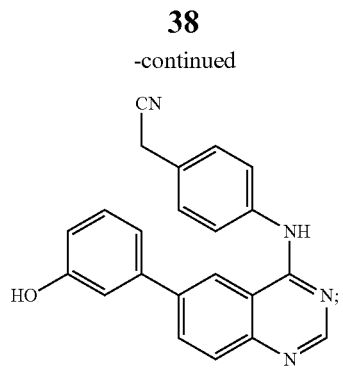
10

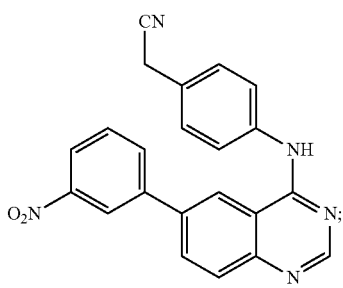
11

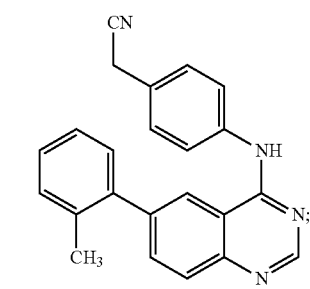
12

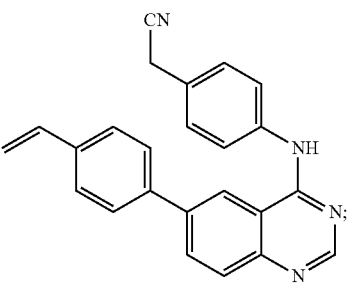
13

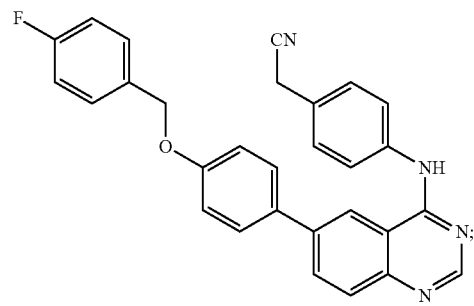
14

16
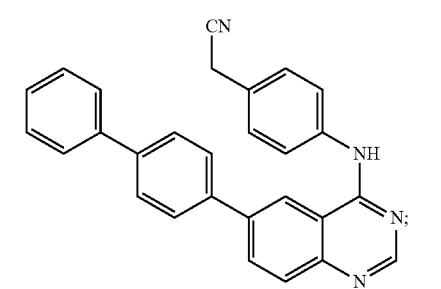
17
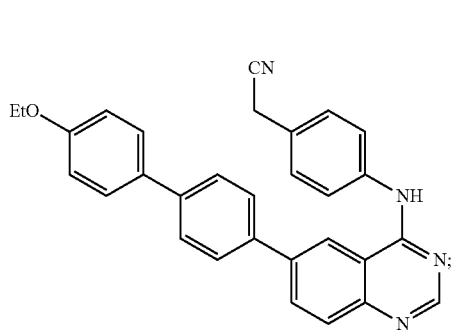
18
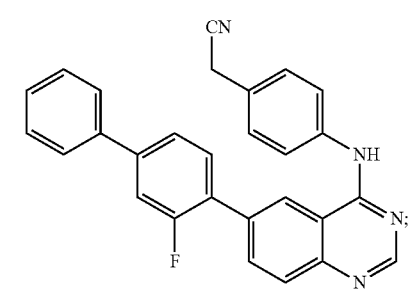
19
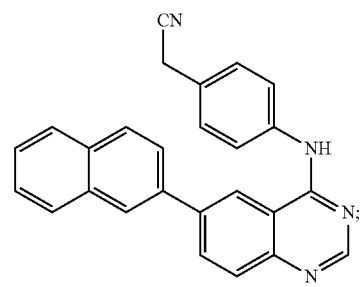
20
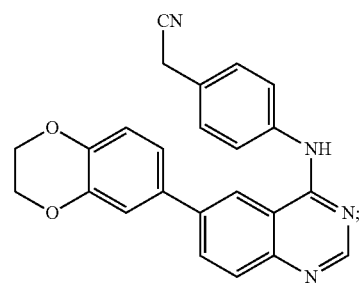
21
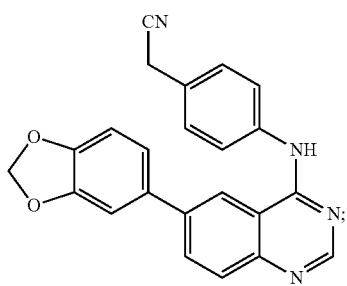
22
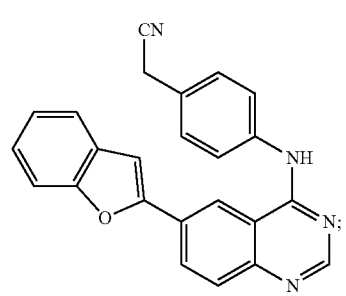
23
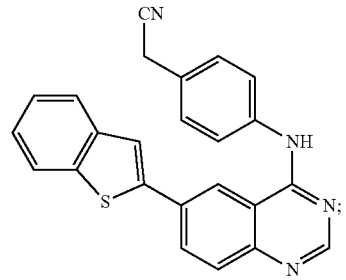
24
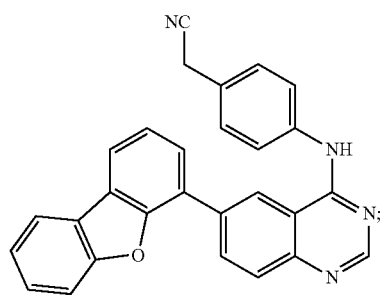
25
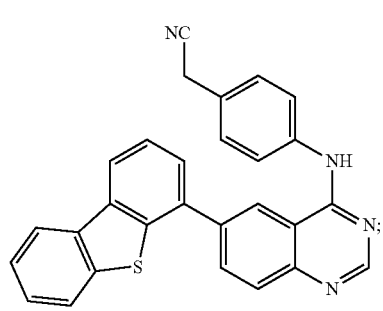

-continued

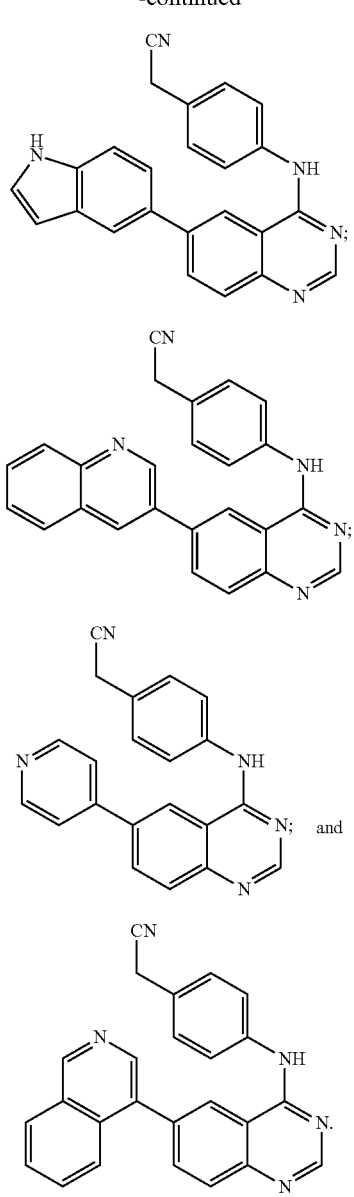

9. The compound of claim 1,
wherein Ar is phenyl, pyridine, quinoline, isoquinoline, naphthalene, 2,3-dihydrobenzo[b][1,4]dioxin, benzo[d][1,3]dioxol, benzofuran, benzo[b]thiophene, dibenzo(b,d)furan, dibenzo(b,d)thiophen, or 1H-indole, each of which is unsubstituted.

10. The compound of claim 1,
wherein Ar is phenyl, pyridine, quinoline, isoquinoline, naphthalene, 2,3-dihydrobenzo[b][1,4]dioxin, benzo[d][1,3]dioxol, benzofuran, benzo[b]thiophene, dibenzo(b,d)furan, dibenzo(b,d)thiophene or 1H-indole, each of which is substituted with one or two R.

11. The compound of claim 1,
wherein Ar is phenyl, pyridine, quinoline, isoquinoline, naphthalene, 2,3-dihydrobenzo[b][1,4]dioxin, benzo[d][1,3]dioxol, benzofuran, benzo[b]thiophene, dibenzo(b,d)furan, dibenzo(b,d)thiophene, or 1H-indole, each of which is unsubstituted or substituted with one or two R, wherein R is alkyl, alkoxy, alkenyl, nitro, fluoro, chloro, bromo, iodo, formyl, allyl, vinyl, benzyl, acetyl, hydroxyl or phenyl.

12. A compound having the structure:

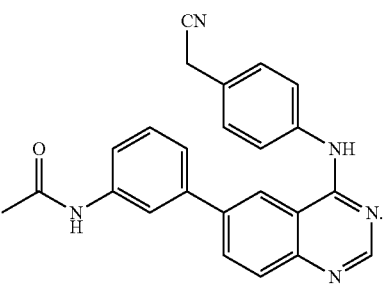

13. A method for selectively inhibiting phosphatoinositide 3-kinase-alpha enzyme in a human having a human cancer selected from the group consisting of pancreatic, breast, prostate, leukemia, and melanoma cancer comprising administering to the human an effective inhibiting amount of the compound of claim 1.

14. A process for preparing the compound of claim 1, comprising the following process steps:
a) reacting anthranilic acid (1) with bromine in glacial acetic acid at a temperature of 10-25° C. for between 15-30 min, followed by diluting with dilute HCl to obtain monobromo anthranilic acid (2);
b) adding formamide to monobromo anthranilic acid obtained in step (a) followed by reflux at a temperature between 100-150° C. for between 4-10 h to obtain 6-bromoquinazolin-4-ol compound (3);
c) adding POCl₃ to the solution of compound 3 obtained in step (b) followed by reflux at a temperature between 100-150 ° C. for between 4-10 h to obtain 6-bromo-4-chloroquinazoline compound (4);
d) adding 4-amino benzylcyanide to the solution of compound 4 obtained in step (c) to form a mixture which is dissolved in isopropanol followed by stirring for between 2-6 h under reflux at a temperature between 80-100° C. to obtain 6-bromo-4-(4-cyanomethyl)phenylamincquinazoline compound (5); and
e) reacting aryl boronic acid in a suitable solvent with compound 5 as obtained in step (d) followed by addition of Pd(PPh₃)₄ followed by stirring the resultant mixture for between 12-24 h at a temperature between 80-100° C. to yield the compound of formula I,
wherein the aryl in the aryl boronic acid in step (e) is selected form the group consisting of phenyl, pyridine, quinoline, isoquinoline, naphthalene, 2,3-dihydrobenzo[b][1,4]dioxin, benzo[d][1,3]dioxol, benzofuran, benzo[b]thiophene, dibenzo(b,d)furan, dibenzo(b,d)thiophene, or 1H-indole, each of which is unsubstituted or substituted with one or two R.

15. The process of claim 14, wherein the aryl boronic acid in step (e) is selected form the group consisting of substituted phenyls, substituted biphenyls and substituted naphthyls.

16. The process of claim 14, wherein the suitable solvent in step (e) is toluene or dioxane.

* * * * *